United States Patent
Nagasawa et al.

(10) Patent No.: US 7,524,980 B2
(45) Date of Patent: Apr. 28, 2009

(54) VITAMIN $D_3$ LACTAM DERIVATIVE

(75) Inventors: Kazuo Nagasawa, Tokyo (JP); Yuichi Hashimoto, Tokyo (JP); Yuko Kato, Hino (JP)

(73) Assignee: Teijin Pharma Limited, Tokyo (JP)

( * ) Notice: Subject to any disclaimer, the term of this patent is extended or adjusted under 35 U.S.C. 154(b) by 938 days.

(21) Appl. No.: 10/980,253

(22) Filed: Nov. 4, 2004

(65) Prior Publication Data

US 2005/0182032 A1    Aug. 18, 2005

Related U.S. Application Data

(60) Provisional application No. 60/516,727, filed on Nov. 4, 2003.

(51) Int. Cl.
*C07C 401/00* (2006.01)
*C07C 403/00* (2006.01)
*C07D 207/00* (2006.01)
*A01N 45/00* (2006.01)
*A61K 31/59* (2006.01)

(52) U.S. Cl. .................. 552/653; 548/552; 514/167

(58) Field of Classification Search ............. 552/653; 548/543; 514/167
See application file for complete search history.

(56) References Cited

U.S. PATENT DOCUMENTS 6,531,460 B1    3/2003    Takenouchi et al.

FOREIGN PATENT DOCUMENTS

JP    2002-069003 A    3/2002
WO    00/24712 A1    5/2000

OTHER PUBLICATIONS

Yuko Kato, et al., Novel Heteroatom-containing Vitamin $D_3$ Analogs: Efficient Synthesis of 1α,25-Dihydroxyviatmin $D_3$-26,23-lactam, Molecules, 2003, vol. 8, No. 6, pp. 488-499.

Kato, Yuko et al., "Research on the creation of novel nitrogen-containing nuclear receptor (VDR, AR) ligands," Abstracts of the 22nd Symposium on Medicinal Chemistry (Shizuoka), 11th Annual Meeting of the Division of Medicinal Chemistry of the Pharmaceutical Society of Japan, Nov. 5, 2002 pp. 272-273, ISSN 0919-214X.
Y. Kato, et al., "Synthesis of 1alpha,25-dihydroxyvitamin D3-26,23-lactams (DLAMs), a novel series of 1alpha,25-dihydroxyvitamin D3 antagonist", Bioorganic & Medicinal Chemistry Letters, vol. 14, pp. 2579-2583, 2004.

*Primary Examiner*—Sreeni Padmanabhan
*Assistant Examiner*—Kara R McMillian
(74) *Attorney, Agent, or Firm*—Sughrue Mion, PLLC

(57) ABSTRACT

Compounds expressed by the following formula (1) or pharmaceutically permissible solvate thereof which is effective for treating Paget's disease of bone, hypercalcemia or osteoporosis.

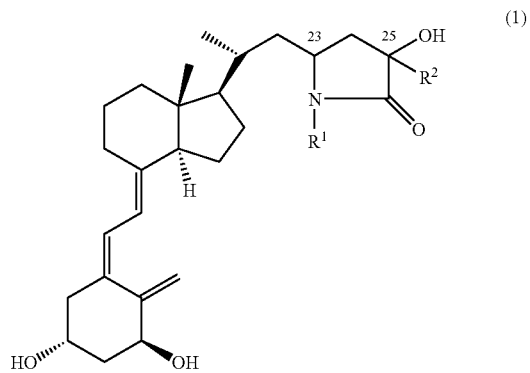

In the formula, $R^1$ is a $C_2$-$C_{10}$ alkyl group, or a $C_7$-$C_{15}$ aralkyl group whose aromatic ring is optionally substituted with a $C_1$-$C_6$ alkyl group, a $C_1$-$C_6$ alkoxyl group, a hydroxyl group, a halogen atom or a trifluoromethyl group; and $R^2$ is a $C_1$-$C_{10}$ alkyl group, or a $C_7$-$C_{15}$ aralkyl group whose aromatic ring is optionally substituted with a $C_1$-$C_6$ alkyl group, a $C_1$-$C_6$ alkoxyl group, a hydroxyl group, a halogen atom or a trifluoromethyl group.

8 Claims, No Drawings

VITAMIN D₃ LACTAM DERIVATIVE

This application claims benefit of Provisional Application No. 60/516,727 filed Nov. 4, 2003. This application enjoys the benefit of a national priority based on U.S. provisional application No. 60/516,727 filed on the 4 of Nov. 2003.

TECHNICAL FIELD

The present invention relates to a vitamin $D_3$ lactam derivative useful as a pharmaceutical agent or a pharmaceutically permissible solvate thereof. More particularly, it relates to a vitamin $D_3$ lactam derivative effective for treating one or plurality of diseases out of osteoporosis, hypercalcemia and Paget's disease of bone, or a pharmaceutically permissible solvate thereof.

BACKGROUND ART

Paget's disease of bone is a disease of unknown etiology in which bone resorption is abnormally accelerated in the pelvis, the femur, the skull, etc., and thereby symptoms such as bone deformation and ostealgia develop. Treating agents presently used for Paget's disease of bone are bisphosphonate formulations and calcitonin formulations, which are also used as osteoporosis treating agents. But, the former has poor taking compliance since the necessary administration dose is 4 to 5 times the administration dose for an osteoporosis patient, and the later has a disadvantageous point that sufficient suppression of bone resorption is not exhibited. Further, these formulations are nosotropic drugs resting on the basis of the bone resorption suppressing activity of the agents and can not completely cure the disease.

It has recently been made clear that osteoclast precursor cells collected from a patient of Paget's disease of bone have $1\alpha$, 25-dihydroxyvitamin $D_3$ receptors, and the sensitivity of the precursor cells to $1\alpha,25$-dihydroxyvitamin $D_3$ is stronger by 10 to 100 times that of the osteoclast precursor cells in a normal person (J. Bone Miner. Res., 15, 228-236 (2000)). Further, the blood concentration of $1\alpha$, 25-dihydroxyvitamin $D_3$ in a patient of Paget's disease of bone being same as in a normal person, the sthenia of bone resorption by endogenic $1\alpha$, 25-dihydroxyvitamin $D_3$ is supposed to play an important role to the onset of Paget's disease of bone. Thus, a compound which suppresses the action of $1\alpha,25$-dihydroxyvitamin $D_3$ on osteoclast precursor cells, that is, a compound like a vitamin D antagonist, can suppress the bone resorption accelerated in a patient of Paget's disease of bone more completely, and it is expected that the compound has a therapeutic effect superior to that of a presently used bone resorption-suppressing agent.

On the other hand, hypercalcemia develops when vitamin D production is accelerated by various kinds of diseases such as lymphoma (Blood, vol. 82, 1383-1394 (1993)), tuberculosis (N. Ingl. J. Med., vol. 311, 1683-1685 (1984)), sarcoidosis (J. Clin. Endocrinol. Metab., vol. 60, 960-966 (1985)), candidosis (Am. J. Med., vol. 74, 721-724 (1983), granuloma (Am. J. Nephrol., vol. 13, 275-277 (1993)), leprosy (Ann. Intern Med., vol. 105, 890-891 (1986)), primary hyperparathyroidism and a malignant tumor. Since it is known that the blood calcium concentration is increased by the action of an active vitamin $D_3$, a compound antagonistic to the action of an active vitamin $D_3$, that is, a vitamin $D_3$ antagonist is considered to be effective for treating hypercalcemia.

Further, a vitamin $D_3$ antagonist is considered to be effective also as a treating agent for osteoporosis. In this disease, the bone quantity decreases as a result of bone resorption overcoming osteogenesis, and this disease often develops after menopause or with aging. A bisphosphonate, a vitamin $D_3$ derivative, estrogen, calcitonin or the like is used as a treating agent for osteoporosis. Further, a parathyroid hormone (PTH) formulation which has such strong osteogenesis stimulating effect as not observed heretofore has appeared on clinical fields recently, and it becomes possible for patients of osteoporosis to receive more effective pharmacotherapy. However, being an injection, the PTH formulation has troubles in convenience, drug compliance, price and the like. Accordingly, if an agent which is not expensive can have an activity equivalent to PTH by oral administration, it may become a useful agent. Incidentally, the secretion of PTH is controlled by blood calcium or $1\alpha,25$-dihydroxyvitamin $D_3$, an active vitamin $D_3$, and the quantity of the secretion of PTH increases with decreasing concentration of such a component. Hence, a compound which is antagonistic to the activity of $1\alpha,25$-dihydroxyvitamin $D_3$, that is, a vitamin $D_3$ antagonist accelerates PTH secretion, and it is expected for the compound to exhibit an effect similar to the above mentioned PTH formulation.

By the way, in the abstract (published on Nov. 5, 2002) of the $22^{nd}$ symposium on medicinal chemistry and the $11^{th}$ annual meeting of division of medicinal chemistry in the Pharmaceutical Society of Japan, a pair of compounds which are expressed by the below-mentioned formula (1) were disclosed. One compound has $R^1=R^2=Me$, and the other compound has $R^1=Bn$ and $R^2=Me$, in the formula. However, the former is not included in the present invention, and the disclosure of the latter was made by the inventors of the present invention, and the above-mentioned provisional application, on which the present invention is based, had been made within one year from the disclosure. Therefore, the novelty of the present invention is not rejected. Further, in the disclosure, there was no suggestion on the vitamin $D_3$ antagonist activity.

Further, in the description of International Publication WO00/24712, vitamin $D_3$ derivatives having a lactam structure on the side chain were disclosed. However, their chemical structures are different from the compounds of the present invention in that the nitrogen atom in the lactone ring is not substituted, and the substituents of the 25-position do not include a hydroxyl group. The antagonist activity to a vitamin $D_3$ was not suggested also in this disclosure.

As vitamin $D_3$ derivatives having an antagonist activity to vitamin $D_3$, compounds described in the descriptions of International Publication WO95/33716, International Publication WO03/070716, International Publication WO94/07853, International Publication WO97/00242 and International Publication WO97/41096 are known. However, they are clearly different from the compounds of the present invention in their chemical structure; that is, the compounds described in the first two have α-ethoxymethylene lactone structures at the side chain, and the compounds described in the last three have 22-ene-24-hydroxy structures at the side chain.

Further, vitamin $D_3$ derivatives having the antagonist activity to vitamin $D_3$ were also disclosed in the description of International Publication WO03/000634; however, they are different from the compounds of the present invention in that the derivatives have ester groups bound to the 1-position.

It is known that vitamin $D_3$ derivatives have various kinds of interesting physiological activities, and variegated vitamin $D_3$ derivatives have been synthesized heretofore by a number of researchers. Nevertheless, antagonist activities to vitamin $D_3$ have been observed only in these three groups which have no commonality to each other and cover a narrow range. That is, it can be said that no findings have been accumulated heretofore regarding relations between chemical structures of vitamin $D_3$ derivatives and antagonist activities to vitamin $D_3$. Even though an antagonist activity to vitamin $D_3$ is observed in a vitamin $D_3$ compound, an antagonist activity to vitamin $D_3$ can not be expected in a compound having a structure slightly different from the compound.

DISCLOSURE OF THE INVENTION

It is an object of the present invention to provide compounds antagonistic to the action of active vitamin $D_3$, that is, vitamin $D_3$ antagonists. Such a vitamin $D_3$ antagonist is considered to be useful as an active ingredient of a treating agent for Paget's disease of bone, hypercalcemia and/or osteoporosis.

The inventors of the present invention carried out studies with the above object, and they reached the below-mentioned invention.

That is, the present invention provides vitamin $D_3$ derivatives expressed by the following formula (1) or pharmaceutically permissible solvate thereof.

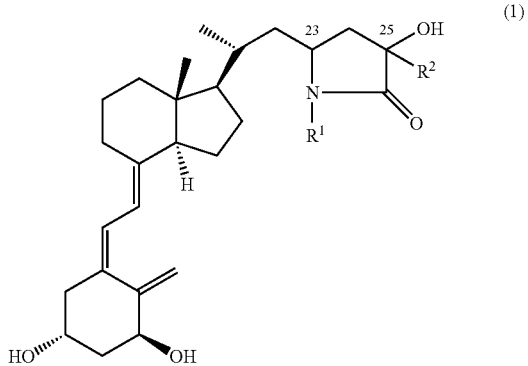

(1)

In the formula, $R^1$ is a $C_2$-$C_{10}$ alkyl group, or a $C_7$-$C_{15}$ aralkyl group whose aromatic ring is optionally substituted with a $C_1$-$C_6$ alkyl group, a $C_1$-$C_6$ alkoxyl group, a hydroxyl group, a halogen atom or a trifluoromethyl group; and $R^2$ is a $C_1$-$C_{10}$ alkyl group, or a $C_7$-$C_{15}$ aralkyl group whose aromatic ring is optionally substituted with a $C_1$-$C_6$ alkyl group, a $C_1$-$C_6$ alkoxyl group, a hydroxyl group, a halogen atom or a trifluoromethyl group.

Configurations of the 23-position and the 25-position in the formula (1) can be either of (S) and (R) configurations, independently. The present invention also includes a mixture of these stereoisomers at an arbitrary ratio.

Further, the present invention provides a method for treating one or plurality of diseases selected from the group consisting of hypercalcemia, Paget's disease of bone and osteoporosis, comprising the step of administering to a patient a therapeutically effective amount of a vitamin $D_3$ derivative expressed by the above formula (1) or a pharmaceutically permissible solvate thereof.

BEST MODE FOR CARRYING OUT THE INVENTION

Terms in the present invention are defined as follows.

An alkyl group is a normal, branched or cyclic aliphatic hydrocarbon group. A $C_2$-$C_{10}$ alkyl group is an alkyl group having a carbon number of 2-10. Concrete examples are an ethyl group, a propyl group, an isopropyl group, a butyl group, an isobutyl group, a pentyl group, an isopentyl group, a hexyl group, an octyl group, a decyl group, a cyclopropyl group, a cyclopropylmethyl group and a cyclohexyl group. In the same manner, for $C_1$-$C_6$ alkyl group, concrete examples are a methyl group, an ethyl group, a propyl group, an isopropyl group, a butyl group, an isobutyl group, a pentyl group, an isopentyl group, a hexyl group, a cyclopropyl group, a cyclopropylmethyl group and a cyclohexyl group; for $C_1$-$C_{10}$ alkyl group, concrete examples are a methyl group, an ethyl group, a propyl group, an isopropyl group, a butyl group, an isobutyl group, a pentyl group, an isopentyl group, a hexyl group, an octyl group, a decyl group, a cyclopropyl group, a cyclopropylmethyl group and a cyclohexyl group.

A $C_1$-$C_6$ alkoxy group is a normal, branched or cyclic aliphatic hydrocarbonoxy group having a carbon number of 1-6. Concrete examples are a methoxy group, an ethoxy group, a propoxy group, an isopropoxy group, a butoxy group, an isobutoxy group, a pentyloxy group, an isopentyloxy group, a hexyloxy group, a cyclopropoxy group, a cyclopropylmethoxy group, a cyclohexyloxy group and the like.

A $C_7$-$C_{15}$ aralkyl group is an aromatic hydrocarbon-substituted normal, branched or cyclic aliphatic hydrocarbon group whose total carbon number is 7-15. Concrete examples are a benzyl group, a phenethyl group, a 3-phenylpropyl group, a 4-phenylbutyl group, a 5-phenylpentyl group, a 1-naphthylmethyl group, a 2-naphthylmethyl group, a 2-(1-naphthyl)ethyl group, a 2-(2-naphthyl)ethyl group, a 3-(1-naphthyl)propyl group, a 3-(2-naphthyl)propyl group, a 4-(1-naphthyl)butyl group, a 4-(2-naphthyl)butyl group, a 5-(1-naphthyl)pentyl group, a 5-(2-naphthyl)pentyl group and the like.

In this description, a benzyl group is sometimes expressed as "Bn".

In the above formula (1), $R^1$ is a $C_2$-$C_{10}$ alkyl group or a $C_7$-$C_{15}$ aralkyl group whose aromatic ring is optionally substituted with one or more substituents selected from the group consisting of a C1-C6 alkyl group, a C1-$C_6$ alkoxy group, a hydroxy group, a halogen atom and a trifluoromethyl group. Among these groups, an isopropyl group, a butyl group, a hexyl group, an octyl group, a benzyl group, a phenethyl group, a 3-phenylpropyl group, a 4-phenylbutyl group, 2-naphthylmethyl group and a 4-methoxybenzyl group are preferable, and a benzyl group, a phenethyl group, a 4-phenylbutyl group and a 4-methoxybenzyl group are especially preferable.

In the above formula (1), $R^2$ is a $C_1$-$C_{10}$ alkyl group, or a $C_7$-$C_{15}$ aralkyl group whose aromatic ring is optionally substituted with one or more substituents selected from the group consisting of a C1-C6 alkyl group, a $C_1$-$C_6$ alkoxy group, a hydroxy group, a halogen atom and a trifluoromethyl group. Among these groups, a methyl group, an ethyl group, an isopropyl group and a benzyl group are preferable, and a methyl group, an ethyl group and a propyl group are especially preferable.

In the above formula (1), configurations of the 23-position and the 25-position are independently (S) or (R) configuration, respectively; however, a compound of 23(R) and 25(R) configurations, and that of 23(S) and 25(S) configurations are preferable, and a compound of 23(S) and 25(S) configurations is especially preferable.

As preferable concrete examples of vitamin $D_3$ derivatives expressed by the formula (1) of the present invention, the compounds shown in the following table can be cited. Further, the configurations of the 23-position and the 25-position of the compounds in the table may be either of (S) configuration and (R) configuration, as far as it is not especially specified.

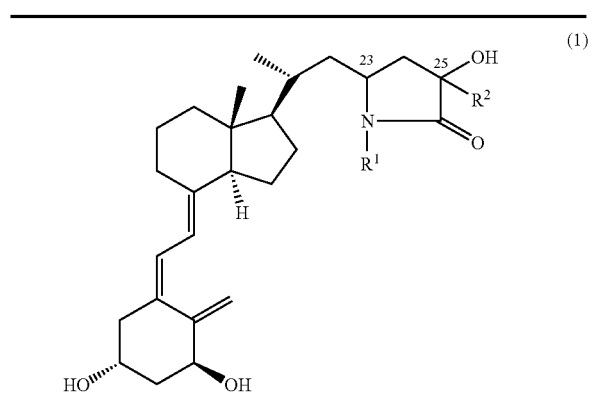

(1)

| Compound No. | R¹ | R² |
|---|---|---|
| 11 | isopropyl | methyl |
| 12 | isopropyl | ethyl |
| 13 | isopropyl | propyl |
| 14 | isopropyl | benzyl |
| 21 | butyl | methyl |
| 22 | butyl | ethyl |
| 23 | butyl | propyl |
| 24 | butyl | benzyl |
| 31 | hexyl | methyl |
| 32 | hexyl | ethyl |
| 33 | hexyl | propyl |
| 34 | hexyl | benzyl |
| 41 | octyl | methyl |
| 42 | octyl | ethyl |
| 43 | octyl | propyl |
| 44 | octyl | benzyl |
| 51 | benzyl | methyl |
| 52 | benzyl | ethyl |
| 53 | benzyl | propyl |
| 54 | benzyl | benzyl |
| 61 | phenethyl | methyl |
| 62 | phenethyl | ethyl |
| 63 | phenethyl | propyl |
| 64 | phenethyl | benzyl |
| 71 | 3-phenylpropyl | methyl |
| 72 | 3-phenylpropyl | ethyl |
| 73 | 3-phenylpropyl | propyl |
| 74 | 3-phenylpropyl | benzyl |
| 81 | 4-phenylbutyl | methyl |
| 82 | 4-phenylbutyl | ethyl |
| 83 | 4-phenylbutyl | propyl |
| 84 | 4-phenylbutyl | benzyl |
| 91 | 2-naphthylmethyl | methyl |
| 92 | 2-naphthylmethyl | ethyl |
| 93 | 2-naphthylmethyl | propyl |
| 94 | 2-naphthylmethyl | benzyl |
| 101 | 4-methoxybenzyl | methyl |
| 102 | 4-methoxybenzyl | ethyl |
| 103 | 4-methoxybenzyl | propyl |
| 104 | 4-methoxybenzyl | benzyl |

The production of a vitamin $D_3$ derivative expressed by the above formula (1) may be preformed by any method; however, it can be produced, for example, according to Scheme 1. That is, compound (2) obtained from vitamin $D_2$ according to a known method (for example, the description of International Publication WO2004/067525) and an $R^1$-bound hydroxylamine are made to react in the presence of triethylamine to obtain a nitron (3). An $R^2$-substituted acrylic ester (4) is added to the nitron (3) to obtain an isoxazolidine derivative (5). In the case where the R is not a methyl group, the R is converted to a methyl group; subsequently, the N—O bond is reduced to form a lactam ring, and finally the TBS group is removed for deprotection to obtain the objective compound (1).

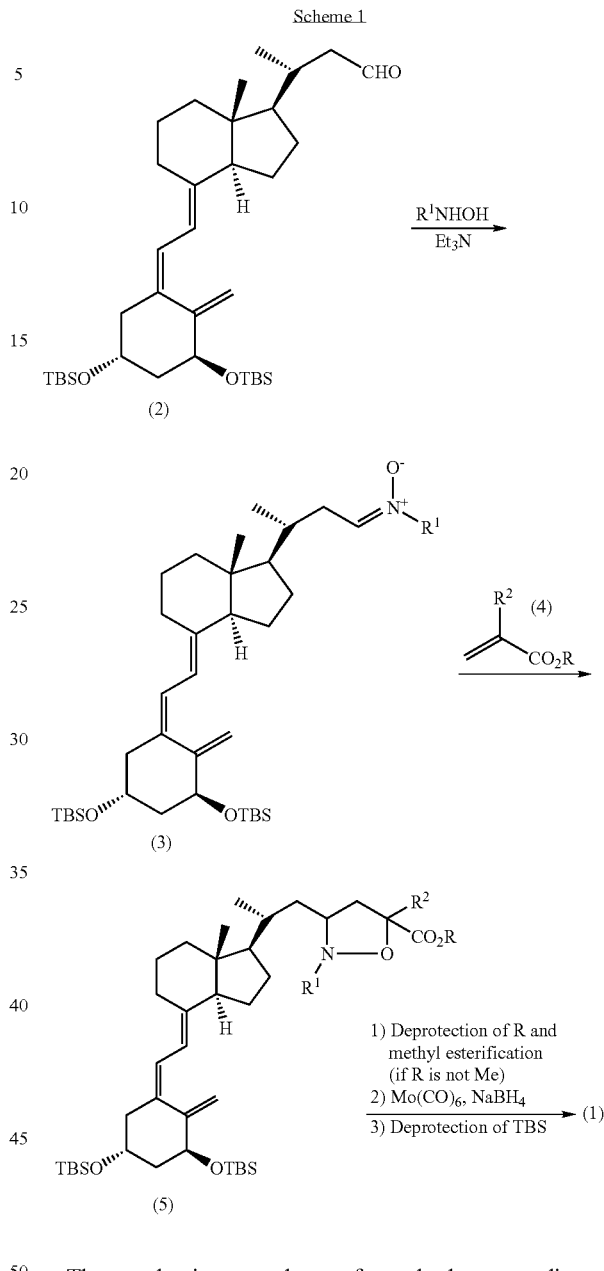

The production can be performed also according to Scheme 2. That is, by using compound (6) which can be produced from vitamin $D_2$ according to a method described in literature (for example, the description of International Publication WO95/33716), similar reactions shown in Scheme 1 are carried out, the hydroxyl group on the lactam ring is protected with a TMS group to obtain a lactam ring-having bromomethylene derivative (9). This compound is subjected to a coupling reaction with ene-yne compound (10) (obtainable by a method described, for example, in Tetrahedron Lett., vol. 35, 8119-8122 (1994)) in the presence of a palladium catalyst according to a method of Trost et al. (J. Am. Chem. Soc., vol. 114, 9836-9845 (1992)) and successively TBS group is removed from the reaction product in a deprotection reaction to obtain the objective compound (1).

Scheme 2

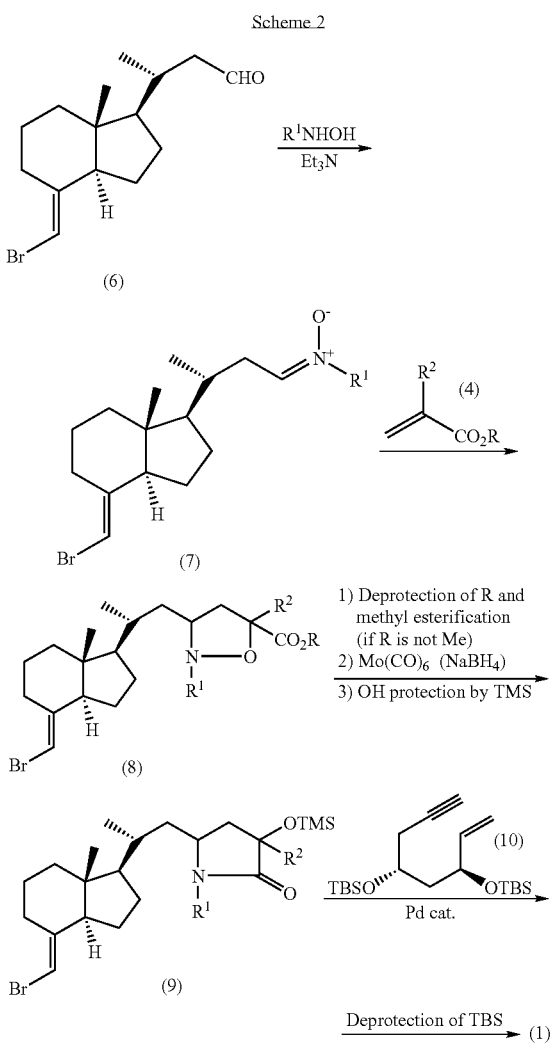

The vitamin $D_3$ derivative obtained through the above-mentioned processes can be converted into a pharmaceutically permissible solvate shown above at need. Examples of the solvent are water, methanol, ethanol, 1-propanol, 2-propanol, butanol, 2-methyl-2-propanol, acetonitrile, acetone, methyl ethyl ketone, chloroform, ethyl acetate, diethyl ether, t-butyl methyl ether, benzene, toluene, DMF, DMSO and the like. Especially, water, methanol, ethanol, 1-propanol, 2-propanol, acetonitrile, acetone, methyl ethyl ketone and ethyl acetate can be cited as preferable examples.

Through conventional pharmaceutical formulation, the compound of the present invention can be administered, as a pharmaceutical active ingredient, orally, or parenterally such as intravenously, subcutaneously, intramuscularly, percutaneously, intranasally or intrarectally, or by inhalation. The therapeutically effective dose of the active ingredient, that is, the compound of the present invention depends on the administration route, the age and sex of the patient, and the conditions of the disease, but it is ordinarily about 0.001-1,000 µg per day, more preferably about 0.01-100 µg per day, and the administration frequency is ordinarily 1-3 times per day. The drug is preferably formulated so as to meet these conditions.

EXAMPLES

Hereafter, the present invention will be explained further in detail with examples; however the present invention is not limited by them. The compound numbers in each example correspond to the compound numbers shown in the above-described table or those in the above Scheme 1 or 2.

Reference Example 1

Production of 2-phenylethylhydroxylamine

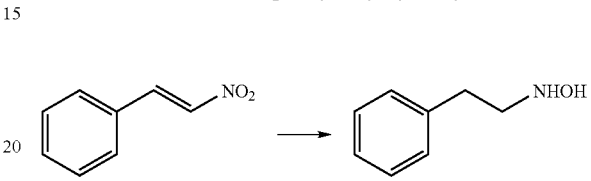

To a THF solution (1.1 mL, 1.0 M) of $BH_3$-THF (1.1 mmol) was added dropwise a THF solution (2.2 mL) of trans-β-nitrostyrene (160.0 mg, 1.1 mmol) at 0° C. under nitrogen atmosphere. $NaBH_4$ (3.3 mg, 0.087 mmol) was added, and the mixture was stirred for 20 minutes at room temperature. Water (5 mL) was added at 0° C., and then the solution was made acidic by adding 2M HCl aqueous solution, and the solution was stirred for 4 hr at 65° C. The reaction mixture was extracted with ethyl acetate, and the aqueous layer was further extracted with ethyl acetate after the addition of 15% NaOH aqueous solution and NaCl. The organic layers were dried over anhydrous magnesium sulfate, filtered and evaporated. The residue was purified by flush column chromatography (chloroform:methanol=1:0→10:1) to obtain the objective substance (62.7 mg, 43%) as white crystals.

$^1$H NMR ($CDCl_3$) δ: 7.47 (brs, 1H), 7.31-7.20 (m, 5H), 3.26 (t, J=7.3 Hz, 2H), 2.97 (t, J=7.3 Hz, 2H).

Reference Example 2

Production of 3-phenylpropylhydroxylamine

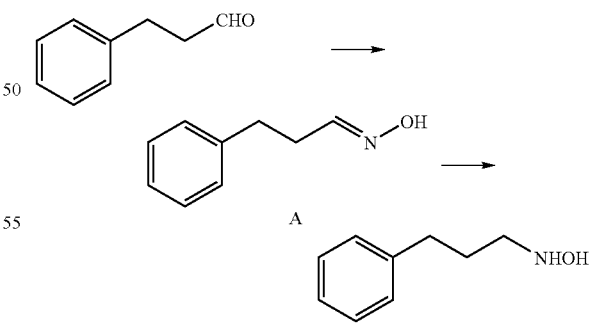

(1) To a dichloromethane solution (5.0 mL) of 3-phenyl-propionaldehyde (0.16 mL, 1.20 mmol) were added hydroxylamine hydrochloride (166.7 mg, 2.40 mmol) and $Et_3N$ (0.7 mL, 5.05 mmol), and the mixture was stirred for 2 hr at room temperature. Saturated sodium bicarbonate solution was added at 0° C., and the mixture was extracted with dichloromethane. The organic layer was dried over anhydrous magnesium sulfate, filtered and evaporated. The residue was purified by flush column chromatography (hexane:ethyl acetate=5:1) to obtain Compound A (190.0 mg, 100%) as white crystals.

$^1$H NMR (CDCl$_3$) δ: 7.47 (t, J=6.0 Hz, 1H), 7.32-7.19 (m, 5H), 6.80 (brs, 1H), 2.83 (dd, J=7.3, 15.0 Hz, 2H), 2.74 (m, 1H), 2.54 (m, 1H).

(2) To a methanol solution (2.0 mL) of Compound A (46.8 mg, 0.31 mmol) was added NaBH$_3$CN (13.8 mg, 0.22 mmol) at room temperature, and the mixture was stirred for 2 hr at room temperature while keeping the pH at 3 by adding 2M HCl-MeOH solution. The reaction mixture was made alkaline by adding 15% NaOH aqueous solution, and then the mixture was extracted with benzene after the addition of sodium chloride. The organic layer was dried over anhydrous magnesium sulfate, filtered and evaporated. The residue was purified by flush column chromatography (chloroform:methanol=1:0→10:1) to obtain the objective substance (30.7 mg, 65%) as white crystals.

$^1$H NMR (CDCl$_3$) δ: 7.31-7.18 (m, 5H), 5.06 (brs, 2H), 2.97 (t, J=7.2 Hz, 2H), 2.67 (t, J=7.7 Hz, 2H), 1.89 (m, 2H).

Reference Example 3

Production of 4-phenylbutylhydroxylamine

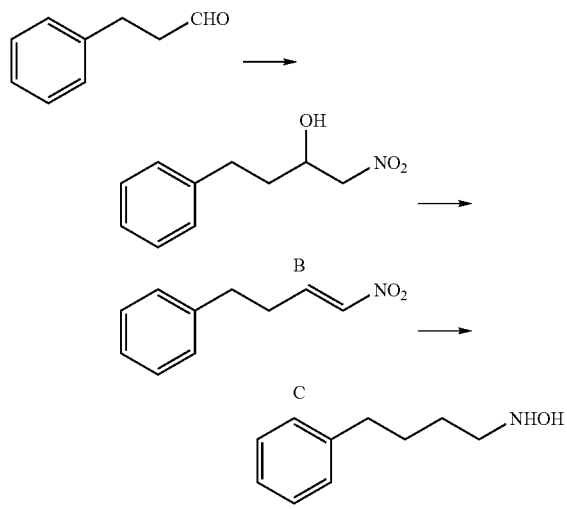

(1) To CH$_3$NO$_2$ (8.1 mL) was added Et$_3$N (0.27 mL, 1.95 mmol) under nitrogen atmosphere, and the mixture was stirred for 5 min at 0° C. 3-Phenylpropionaldehyde (2.0 mL, 15.08 mmol) was added to the resulting mixture at 0° C., and they were stirred for 20 hr. The reaction mixture was diluted with ethyl acetate, and the mixture was washed with saturated sodium bicarbonate solution and brine serially. The organic layer was dried over anhydrous magnesium sulfate, filtered and evaporated. The residue was purified by flush column chromatography (hexane:ethyl acetate=5:1) to obtain Compound B (2.72 g, 93%) as white crystals.

$^1$H NMR (CDCl$_3$) δ: 7.32-7.17 (m, 5H), 4.40 (m, 2H), 4.32 (m, 1H), 2.89-2.72 (m, 2H), 2.60 (brs, 1H), 1.96-1.76 (m, 2H).

(2) To a dichloromethane solution (10.0 mL) of Compound B (500.0 mg, 2.55 mmol) was added Et$_3$N (1.4 mL, 10.1 mmol) under nitrogen atmosphere, MsCl (0.6 mL, 7.7 mmol) was added dropwise at 0° C., and the mixture was stirred for 3 hr at 0° C. The reaction mixture was extracted with ethyl acetate after the addition of water. The organic layer was washed with brine, dried over anhydrous magnesium sulfate and evaporated. The residue was purified by flush column chromatography (hexane:ethyl acetate=20:1) to obtain Compound C (396.1 mg, 88%) as white crystals.

$^1$H NMR (CDCl$_3$) δ: 7.34-7.23 (m, 5H), 7.18 (d, J=7.7 Hz, 1H), 6.96 (d, J=13.3 Hz, 1H), 2.84 (t, J=7.5 Hz, 2H), 2.60 (dd, J=7.5, 14.7 Hz, 2H).

(3) To a 1.02 M BH$_3$-THF solution (2.2 mL, 2.24 mmol) was added dropwise a THF solution (20.0 mL) of Compound C (396.1 mg, 2.24 mmol) at 0° C. under nitrogen atmosphere. NaBH$_4$ (3.0 mg, 0.08 mmol) was added, and the mixture was stirred for 1 hr at room temperature. After water (20 mL) was added at 0° C., the solution was made acidic by adding 2M HCl aqueous solution, and it was stirred for 2 hr at 65° C. The reaction mixture was extracted with ethyl acetate. The water layer was further extracted with ethyl acetate after the addition of 15% NaOH aqueous solution and sodium chloride. The combined organic layers were dried over anhydrous magnesium sulfate, filtered and evaporated. The residue was purified by flush column chromatography (chloroform:methanol=10:1) to obtain the objective substance (286.2 mg, 77%) as white crystals.

$^1$H NMR (CDCl$_3$) δ: 9.88 (brs, 2H), 7.28-7.14 (m, 5H), 3.28 (brs, 2H), 2.63 (t, J=7.6 Hz, 2H), 1.89 (m, 2H), 1.70 (m, 2H).

Reference Example 4

Production of 4-methoxybenzylhydroxylamine

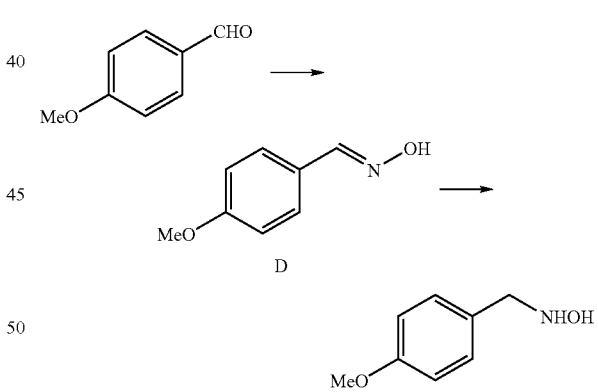

(1) To a dichloromethane solution (50.0 mL) of 4-methoxybenzaldehyde (1.4 mL, 11.57 mmol) were added hydroxylamine hydrochloride (1.39 g, 20 mmol) and Et$_3$N (5.5 mL, 39.68 mmol), and the mixture was stirred for 24 hr at room temperature. Saturated sodium bicarbonate solution was added at 0° C., and the mixture was extracted with dichloromethane. The organic layer was dried over anhydrous magnesium sulfate, filtered and evaporated. The residue was purified by flush column chromatography (chloroform) to obtain Compound D (1.87 g, 100%) as white crystals.

$^1$H NMR (CDCl$_3$) δ: 8.10 (s, 1H), 7.52 (d, J=8.8 Hz, 2H), 6.91 (d, J=8.8 Hz, 2H), 3.84 (s, 3H).

(2) To a methanol solution (1.0 mL) of Compound D (77.8 mg, 0.52 mmol) was added NaBH$_3$CN (22.7 mg, 0.36 mmol) at room temperature. Further, 2M HCl-MeOH solution was added, and the mixture was stirred for 3 hr at room temperature while keeping the pH at 3 by adding 2M HCl-MeOH solution. The reaction mixture was made alkaline by adding 15% NaOH aqueous solution, and then the mixture was extracted with ethyl acetate after the addition of sodium chloride. The organic layer was dried over anhydrous magnesium sulfate, filtered and evaporated. The residue was purified by flush column chromatography (chloroform methanol=1:0→10:1) to obtain the objective substance (73.5 mg, 92%) as white crystals.

$^1$H NMR (CDCl$_3$) δ: 7.25 (d, J=8.6 Hz, 2H), 6.87 (d, J=8.6 Hz, 2H), 4.73 (brs, 2H), 3.97 (s, 2H), 3.80 (s, 3H).

Reference Example 5

Production of Phthalimidemethyl 2-ethylacrylate (Compound (4) (R$^2$=Et, R=Pim))

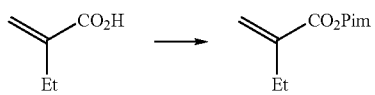

2-Ethylacrylic acid (250 mg, 2.5 mmol) was dissolved in anhydrous dimethylformamide (8.0 mL), to the solution were added N-bromomethylphthalimide (660.0 mg, 2.8 mmol) and potassium fluoride (291.0 mg, 5.0 mmol), and the mixture was stirred for 12 hr at 80° C. under nitrogen atmosphere. The reaction mixture was concentrated in vacuo, and the obtained residue was extracted with dichloromethane after the addition of water (80 mL). The organic layer was dried over magnesium sulfate and concentrated in vacuo, and the resulting residue was purified by silica gel column chromatography (hexane:ethyl acetate=4:1) to obtain the objective substance (463.1 mg, 72%).

$^1$H-NMR (CDCl$_3$) δ: 7.94 (dd, J=5.4, 3.2 Hz, 2H), 7.79 (dd, J=2.8, 1.4 Hz, 2H), 6.16 (d, J=1.0 Hz, 1H), 5.80 (s, 2H), 5.57 (d, J=1.5 Hz, 1H), 2.35-2.25 (m, 2H), 1.06 (t, J=7.4 Hz, 3H).

Reference Example 6

Production of Phthalimidemethyl 2-propylacrylate (Compound (4) (R$^2$=Pr, R=Pim))

A reaction similar to Reference Example 5 was carried out by using 2-propylacrylic acid (300 mg, 2.63 mmol) to obtain the objective substance (643.2 mg, 90%).

$^1$H-NMR (CDCl$_3$) δ: 7.94 (dd, J=5.4, 2.7 Hz, 2H), 7.79 (dd, J=5.4, 2.7 Hz, 2H), 6.16 (d, J=0.7 Hz, 1H), 5.80 (s, 2H), 5.57 (d, J=1.5 Hz, 1H), 2.32-2.23 (m, 2H), 1.55-1.43 (m, 2H), 0.96-0.89 (m, 3H).

Example 1

Production of 1α,25-dihydroxyvitamin D$_3$-26,23-lactam-N-isopropyl (Compound No. 11)

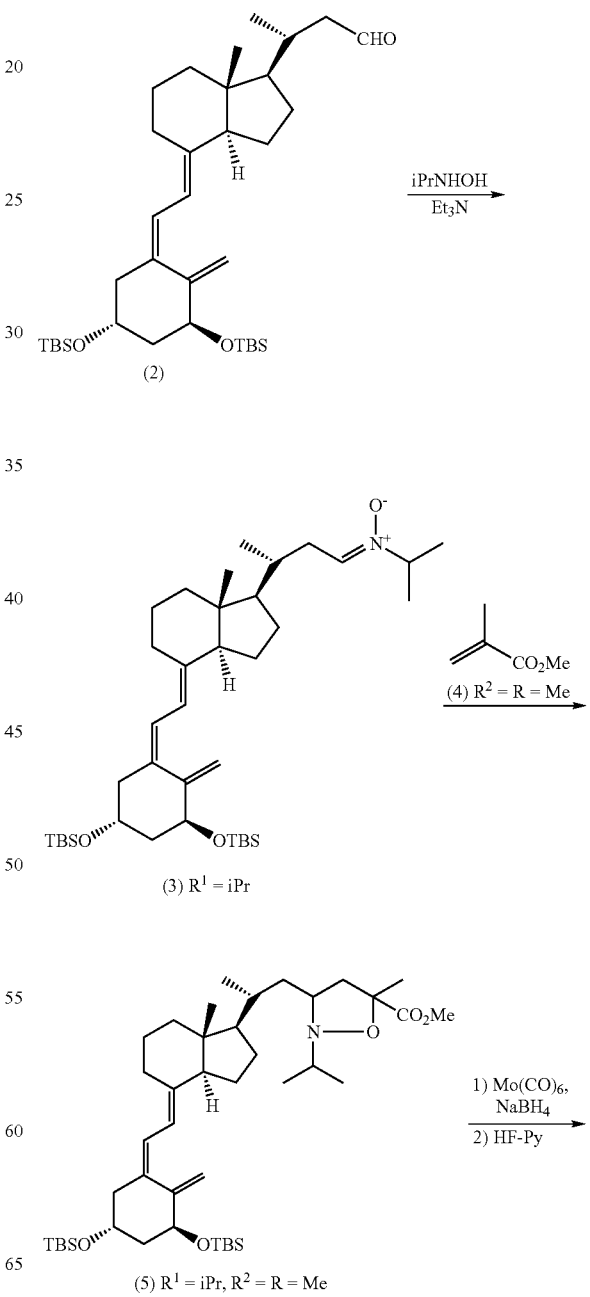

-continued

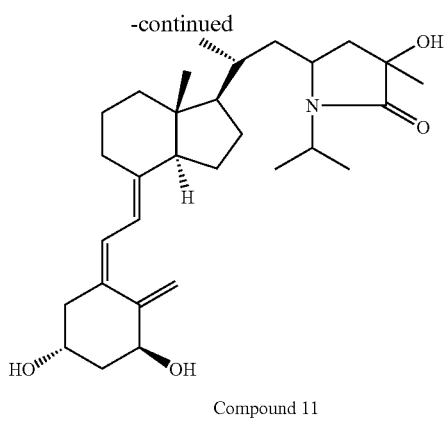

Compound 11

(1) To a dichloromethane solution (2.0 mL) of Compound (2) (53.7 mg, 0.092 mmol) obtained according to a method described in literature (for example, the description of International Publication WO2004/067525) were added isopropylhydroxylamine (20.5 mg, 0.18 mmol) and $Et_3N$ (0.05 mL, 0.36 mmol) under nitrogen atmosphere, and the mixture was stirred for 2 hr at room temperature. The reaction mixture was cooled to 0° C. and extracted with dichloromethane after the addition of saturated $NH_4Cl$ solution. The organic layer was dried over anhydrous magnesium sulfate, filtered and evaporated. The residue was purified by flush column chromatography (hexane:ethyl acetate=10:1→chloroform:methanol=10:1) to obtain Compound (3) ($R^1$=iPr) (47.1 mg, 80%) as a colorless transparent oily substance.

$^1H$ NMR ($CDCl_3$) δ: 6.74 (t, J=5.9 Hz, 1H), 6.23 (d, J=11.0 Hz, 1H), 6.01 (d, J=11.5 Hz, 1H), 5.17 (d, J=1.5 Hz, 1H), 4.85 (d, J=2.4 Hz, 1H), 4.36 (dd, J=3.4, 6.3 Hz, 1H), 4.18 (m, 1H), 4.02 (m, 1H), 2.82 (d, J=12.2 Hz, 1H), 2.57 (m, 1H), 2.44 (d, J=12.9 Hz, 1H), 2.31 (m, 1H), 2.21 (dd, J=7.6, 12.9 Hz, 1H), 2.01-1.25 (m, 14H), 1.41 (d, J=6.3 Hz, 6H), 0.99 (d, J=6.6 Hz, 3H), 0.87 (m, 18H), 0.55 (s, 3H), 0.05 (m, 12H).

(2) To a toluene solution (3.0 mL) of the above obtained Compound (3) ($R^1$=iPr) (47.1 mg, 0.073 mmol) was added methyl methacrylate (Compound (4) ($R^2$=R=Me) (0.078 mL, 0.73 mmol) under nitrogen atmosphere, and the mixture was stirred for 24 hr at 90° C. The reaction mixture was cooled to room temperature, it was evaporated, and the residue was purified by flush column chromatography (hexane:ethyl acetate=50:1→10:1) to obtain Compound (5) ($R^1$=iPr, $R^2$=R=Me) (51.8 mg, 95%) as a colorless transparent oily substance.

$^1H$ NMR ($CDCl_3$) δ: 6.24 (d, J=11.0 Hz), 6.02 (d, J=11.2 Hz), 5.18 (brs), 4.86 (d, J=2.4 Hz), 4.37 (m), 4.20 (m), 3.74 (m), 3.25 (m), 3.12 (dd, J=7.3, 12.7 Hz), 3.01-2.93 (m), 2.80 (m), 2.45 (m), 2.22 (dd, J=7.6, 12.9 Hz), 2.02-0.94 (m), 1.51 (m), 0.89 (m) 0.55 (m), 0.07 (m).

(3) The above obtained Compound (5) ($R^1$=iPr, $R^2$=R=Me) (51.8 mg, 0.070 mmol) was dissolved in a mixed solvent (3.5 mL) of acetonitrile and water (7:1), to the solution were added molybdenumhexacarbonyl (66.7 mg, 0.25 mmol) and $NaBH_4$ (0.5 mg, 0.013 mmol), and the mixture was refluxed for 4 hr at 90° C. under heating. The reaction mixture was filtered through celite, the filtrate was evaporated, and the residue was purified by flush column chromatography (chloroform:methanol=1:0→10:1) to obtain a lactam cyclic compound (23.9 mg, 48%) as a colorless transparent oily substance.

$^1H$ NMR ($CDCl_3$) δ: 6.24 (d, J=11.0 Hz), 6.02 (d, J=10.7 Hz), 5.18 (s), 4.86 (s), 4.38 (m), 4.19 (m), 3.96-3.16 (m), 2.83 (d, J=12.2 Hz), 2.45 (d, J=13.4 Hz), 2.36-1.26 (m), 1.00 (m), 0.88 (m), 0.54 (m), 0.07 (m).

To a THF solution (3.0 mL) of the obtained lactam cyclic compound (40.5 mg, 0.083 mmol) was added HF•Py (2 mL) at 0° C., and the mixture was stirred for 3 hr. The reaction mixture was diluted with ethyl acetate, and solid sodium bicarbonate and saturated sodium bicarbonate solution were added. The mixture was extracted with ethyl acetate, and the organic layer was washed with brine, dried over anhydrous magnesium sulfate, filtered and evaporated. The residue was purified by flush column chromatography (chloroform:methanol=1:0→10:1) to obtain Compound No. 11 (16.6 mg, 60%) as a colorless transparent oily substance. Thus obtained Compound No. 11 (18.8 mg) was subjected to reverse phase HPLC (ODS column, moving phase: A=95% $H_2O$/$CH_3CN$, B=0.5% $H_2O$/60% $CH_3CN$/MeOH; B=75%) to isolate and purify the diastereomers. Thus, Compound No. 11a (23S, 25S body) (1.6 mg, 5.1%), Compound No. 11b (23R, 25R body) (1.8 mg, 5.8%), Compound 11c (23S, 25R body) (1.9 mg, 6.1%) and Compound 11d (23R, 25S body) (2.2 mg, 7.1%) were respectively obtained.

Compound No. 11a:
$^1H$-NMR ($CDCl_3$) δ: 6.38 (d, J=11.5 Hz, 1H), 6.03 (d, J=11.2 Hz, 1H), 5.33 (s, 1H), 5.00 (s, 1H), 4.44 (brs, 1H), 4.24 (brs, 1H), 4.02-3.92 (m, 1H), 3.73-3.63 (m, 1H), 2.87-2.80 (m, 1H), 2.64-2.21 (m, 4H), 2.07-1.22 (m, 25H), 1.00 (d, J=5.9 Hz, 3H), 0.59 (s, 3H).

Compound No. 11b:
$^1H$-NMR ($CDCl_3$) δ: 6.38 (d, J=11.2 Hz, 1H), 6.03 (d, J=10.7 Hz, 1H), 5.33 (s, 1H), 5.00 (s, 1H), 4.44 (brs, 1H), 4.24 (brs, 1H), 3.95-3.84 (m, 1H), 3.66-3.55 (m, 1H), 2.88-2.80 (m, 1H), 2.65-2.26 (m, 4H), 2.08-1.08 (m, 25H), 1.02 (d, J=6.3 Hz, 3H), 0.65 (s, 3H).

Compound No. 11c:
$^1H$-NMR ($CDCl_3$) δ: 6.38 (d, J=11.2 Hz, 1H), 6.02 (d, J=11.5 Hz, 1H), 5.34 (s, 1H), 5.00 (s, 1H), 4.44 (brs, 1H), 4.24 (brs, 1H), 3.97-3.88 (m, 1H), 3.60-3.49 (m, 1H), 2.87-2.80 (m, 1H), 2.63-2.53 (m, 2H), 2.32 (dd, J=12.6, 6.7 Hz, 1H), 2.20 (dd, J=12.6, 6.7 Hz, 1H), 2.05-1.20 (m, 25H), 0.99 (d, J=6.3 Hz, 3H), 0.57 (s, 3H).

Compound No. 11d:
$^1H$-NMR ($CDCl_3$) δ: 6.38 (d, J=11.2 Hz, 1H), 6.03 (d, J=11.2 Hz, 1H), 5.33 (s, 1H), 5.00 (s, 1H), 4.43 (brs, 1H), 4.23 (brs, 1H), 3.89-3.80 (m, 1H), 3.48-3.40 (m, 1H), 2.87-2.80 (m, 1H), 2.63-2.50 (m, 2H), 2.32 (dd, J=12.7, 6.5 Hz, 1H), 2.25 (dd, J=12.7, 6.8 Hz, 1H), 2.10-1.15 (m, 25H), 1.03 (d, J=6.6 Hz, 3H), 0.57 (s, 3H).

Example 2

Production of 1α,25-dihydroxyvitamin $D_3$-26,23-lactam-N-benzyl (Compound No. 51)

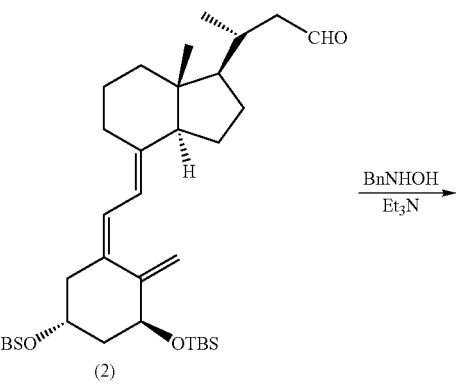

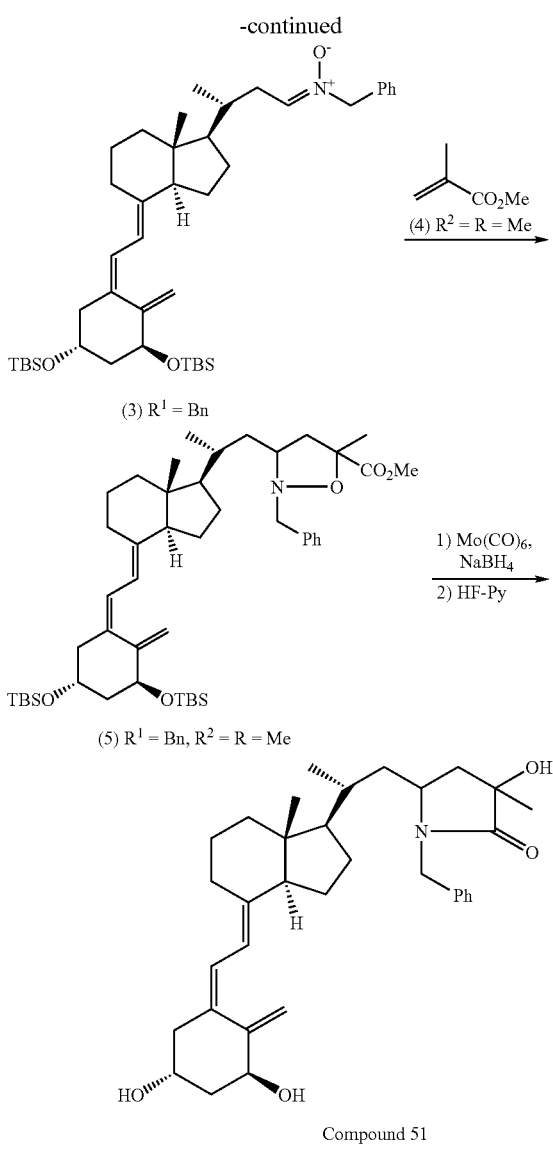

(1) By using Compound (2) (63.3 mg, 0.11 mmol) and benzylhydroxylamine (35.0 mg, 0.22 mmol), a process similar to Example 1(1) was carried out to obtain Compound (3) ($R^1$=Bn) (77.7 mg, 100%) as colorless transparent oily substance.

$^1$H NMR (CDCl$_3$) δ: 7.39-7.32 (m, 5H), 6.78 (brs, 1H), 6.22 (d, J=11.0 Hz, 1H), 6.00 (d, J=11.0 Hz, 1H), 5.17 (s, 1H), 4.94 (brs, 2H), 4.85 (m, 1H), 4.36 (m, 1H), 4.18 (m, 1H), 2.81 (d, J=11.2 Hz, 1H), 2.43 (d, J=12.8 Hz, 1H), 2.21 (m, 1H), 1.96-1.19 (m, 16H), 0.94-0.87 (m, 21H), 0.51 (s, 3H), 0.05 (s, 12H).

(2) The above obtained Compound (3) ($R^1$=Bn) (77.7 mg, 0.12 mmol) was subjected to a process similar to Example 1(2) to obtain Compound (5) ($R^1$=Bn, $R^2$=R=Me) (68.0 mg, 77%) as a colorless transparent oily substance.

$^1$H NMR (CDCl$_3$) δ: 7.40-7.31 (m), 6.23 (d, J=10.0 Hz), 6.01 (d, J=10.8 Hz), 5.18 (m), 4.86 (m), 4.38 (m), 4.19 (m), 4.13-3.88 (m), 3.76 (s), 3.13-1.26 (m), 0.89 (s), 0.69 (d, J=6.1 Hz), 0.54-0.50 (m), 0.06 (s).

(3) The above obtained Compound (5) ($R^1$=Bn, $R^2$=R=Me) (41.0 mg, 0.052 mmol) was subjected to a process similar to Example 1(3) to obtain a lactam cyclic compound (21.7 mg, 55%) as colorless transparent oily substance.

$^1$H NMR (CDCl$_3$) δ: 7.38-7.20 (m), 6.23-6.21 (m), 6.02-5.99 (m), 5.18 (s), 4.86 (m), 4.37 (m), 4.19 (m), 4.09 (d, J=15.0 Hz), 3.98 (d, J=15.0 Hz), 3.52 (m), 3.30 (m), 2.81 (m), 2.43 (m), 2.27-1.25 (m), 1.10-0.87 (m), 0.54-0.46 (m), 0.10-0.06 (m).

The obtained lactam cyclic compound (21.7 mg, 0.029 mmol) was subjected to a process similar to Example 1(3) (diastereomer isolation was performed by normal phase HPLC (silica column, moving phase: hexane/ethyl acetate/2-propanol=35/52/13 or hexane/ethyl acetate/2-propanol=51/45/4) to obtain Compound No. 51a (23S, 25S body) (2.3 mg, 15%), Compound No. 51b (23R, 25R body) (2.3 mg, 15%), Compound No. 51c (23S, 25R body) (1.5 mg, 9.9%) and Compound No. 51d (23R, 25S body) (0.6 mg, 3.8%), respectively.

Compound No. 51a:

$[α]^{24}_D$=+3.54 (c 0.20, CHCl$_3$) $^1$H NMR (CDCl$_3$) δ: 7.33-7.22 (m, 5H), 6.37 (d, J=11.5 Hz, 1H), 6.01 (d, J=11.1 Hz, 1H), 5.32 (s, 1H), 4.99 (s, 1H), 4.97 (d, J=11.1 Hz, 1H), 4.43 (m, 1H), 4.23 (m, 1H), 3.97 (d, J=12.0 Hz, 1H), 3.51 (m, 1H), 2.82 (d, J=12.4 Hz, 1H), 2.59 (d, J=10.3 Hz, 1H), 2.32 (dd, J=6.4, 13.7 Hz, 1H), 2.27 (dd, J=7.7, 13.7 Hz, 1H), 2.05-1.84 (m, 5H), 1.66 (dd, J=5.1, 13.3 Hz, 1H), 1.68-1.17 (m, 12H), 1.49 (s, 3H), 0.88 (m, 2H), 0.77 (d, J=6.0 Hz, 3H), 0.53 (s, 3H).

Compound No. 51b:

$[α]^{24}_D$=+13.73 (c 0.32, CHCl$_3$) $^1$H NMR (CDCl$_3$) δ: 7.33-7.18 (m, 5H), 6.36 (d, J=11.1 Hz, 1H), 6.00 (d, J=11.1 Hz, 1H), 5.34 (s, 1H), 5.00 (s, 1H), 4.98 (d, J=15.0 Hz, 1H), 4.44 (m, 1H), 4.23 (m, 1H), 4.06 (d, J=15.4 Hz, 1H), 3.50 (m, 1H), 2.81 (d, J=12.8 Hz, 1H), 2.60 (d, J=9.8 Hz, 1H), 2.48 (brs, 1H), 2.36 (dd, J=7.7, 13.3 Hz, 1H), 2.31 (dd, J=6.4, 13.3 Hz, 1H), 2.04 (m, 1H), 1.92 (m, 3H), 1.77 (dd, J=5.1, 13.3 Hz, 1H), 1.66-1.20 (m, 11H), 1.50 (s, 3H), 1.03 (m, 2H), 0.88 (m, 1H), 0.86 (d, J=6.4 Hz, 3H), 0.48 (s, 3H).

Compound No. 51c:

$[α]^{24}_D$=+13.75 (c 0.155, CHCl$_3$) $^1$H NMR (CDCl$_3$) δ: 7.34-7.18 (m, 5H), 6.36 (d, J=11.1 Hz, 1H), 6.00 (d, J=11.5 Hz, 1H), 5.32 (s, 1H), 5.00 (d, J=14.5 Hz, 1H), 4.99 (s, 1H), 4.43 (m, 1H), 4.23 (m, 1H), 4.06 (d, J=15.2 Hz, 1H), 3.27 (m, 1H), 2.82 (d, J=12.4 Hz, 1H), 2.76 (brs, 1H), 2.60 (d, J=13.5 Hz, 1H), 2.33 (m, 1H), 2.21 (dd, J=6.4, 12.8 Hz, 1H), 2.19-1.95 (m, 5H), 1.73 (dd, J=8.1, 12.8 Hz, 1H), 1.68-1.20 (m, 12H), 1.35 (s, 3H), 0.88 (m, 4H), 0.76 (d, J=6.4 Hz, 3H), 0.51 (s, 3H).

Compound No. 51d:

$[α]^{24}_D$=−11.38 (c 0.058, CHCl$_3$) $^1$H NMR (CDCl$_3$) δ: 7.33-7.14 (m, 5H), 6.36 (d, J=11.1 Hz, 1H), 6.00 (d, J=11.5 Hz, 1H), 5.33 (s, 1H), 5.01 (d, J=15.0 Hz, 1H), 4.99 (s, 1H), 4.43 (m, 1H), 4.23 (m, 1H), 4.06 (d, J=15.2 Hz, 1H), 3.28 (m, 1H), 2.81 (d, J=12.8 Hz, 1H), 2.68 (brs, 1H), 2.60 (d, J=16.7 Hz, 1H), 2.32 (m, 1H), 2.27 (dd, J=6.4, 12.8 Hz, 1H), 2.17-

1.92 (m, 5H), 1.87 (dd, J=8.1, 12.8 Hz, 1H), 1.75-1.22 (m, 11H), 1.39 (s, 3H), 1.06 (m, 2H), 0.87 (d, J=6.4 Hz, 3H), 0.48 (s, 3H).

Example 3

Production of 1α,25-dihydroxyvitamin D$_3$-26,23-lactam-N-(2-phenethyl) (Compound No. 61)

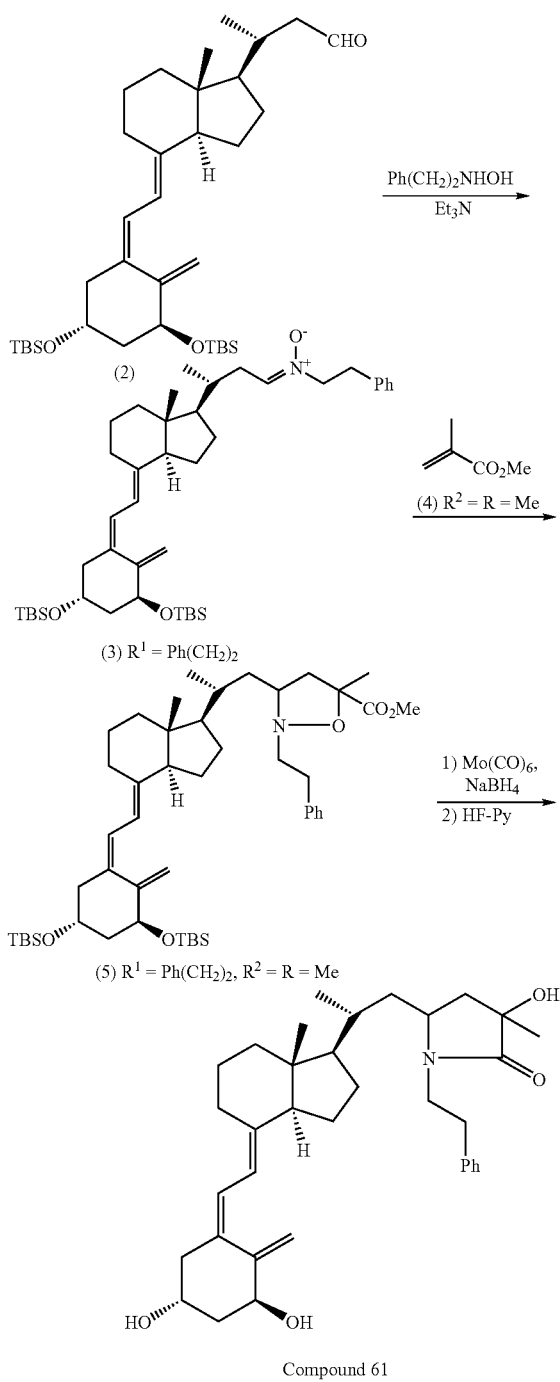

(1) By using Compound (2) (27.4 mg, 0.047 mmol) and 2-phenethylhydroxylamine (13.0 mg, 0.095 mmol) obtained in Reference Example 1, a process similar to Example 1 (1) was carried out to obtain Compound (3) (R$^1$=Ph(CH$_2$)$_2$) (33.5 mg, 100%) as colorless transparent oily substance.

$^1$H NMR (CDCl$_3$) δ: 7.30-7.20 (m, 5H), 6.38 (brs, 1H), 6.23 (d, J=11.1 Hz, 1H), 6.01 (d, J=11.1 Hz, 1H), 5.18 (s, 1H), 4.86 (d, J=2.6 Hz, 1H), 4.37 (dd, J=3.4, 6.8 Hz, 1H), 4.19 (m, 1H), 3.96 (t, J=6.6 Hz, 2H), 3.21 (m, 2H), 2.82 (d, J=12.4 Hz, 1H), 2.44 (m, 2H), 2.23 (m, 2H), 1.95-1.17 (m, 14H), 0.87 (s, 18H), 0.79 (d, J=6.8 Hz, 3H), 0.50 (s, 3H), 0.06 (s, 12H).

(2) The above obtained Compound (3) (R$^1$=Ph(CH$_2$)$_2$) (73.5 mg, 0.104 mmol) was subjected to a process similar to Example 1(2) to obtain Compound (5) (R$^1$=Ph(CH$_2$)$_2$, R$^2$=R=Me) (75.7 mg, 90%) as a colorless transparent oily substance.

$^1$H NMR (CDCl$_3$) δ: 7.28-7.19 (m), 6.23 (d, J=11.1 Hz), 6.02 (d, J=11.1 Hz), 5.18 (s), 4.86 (s), 4.38 (m), 4.19 (m), 3.78-3.76 (m), 3.08-1.24 (m), 0.94-0.88 (m) 0.53-0.50 (m), 0.06 (s).

(3) The above obtained Compound (5) (R$^1$=Ph(CH$_2$)$_2$, R$^2$=R=Me) (75.7 mg, 0.094 mmol) was subjected to a process similar to Example 1(3) to obtain a lactam cyclic compound (28.8 mg, 40%) as colorless transparent oily substance.

$^1$H NMR (CDCl$_3$) δ: 7.31-7.19 (m), 6.23 (d, J=10.7 Hz), 6.02-6.00 (m), 5.19-5.18 (m), 4.87-4.86 (m), 4.38 (m), 4.19 (m), 4.01-3.76 (m), 3.49 (m), 3.28 (m), 3.20-3.07 (m), 2.93-2.72 (m), 2.45 (d, J=11.3 Hz), 2.35-1.14 (m), 0.98-0.87 (m), 0.56-0.52 (m), 0.08-0.06 (m).

The obtained lactam cyclic compound (28.8 mg, 0.037 mmol) was subjected to a process similar to Example 1(3) (diastereomer isolation was performed by normal phase HPLC (silica column, moving phase: hexane/ethyl acetate/2-propanol=35/52/13 or hexane/ethyl acetate/2-propanol=14/81/5) to obtain Compound No. 61a (23S, 25S body) (5.2 mg, 26%), Compound No. 61b (23R, 25R body) (5.7 mg, 28%), Compound No. 61c (23S, 25R body) (1.6 mg, 7.9%) and Compound No. 61d (23R, 25S body) (2.2 mg, 11%), respectively.

Compound No. 61a:
[α]$^{24}_D$=+11.78 (c 0.52, CHCl$_3$) $^1$H NMR (CDCl$_3$) δ: 7.31-7.21 (m, 5H), 6.37 (d, J=11.1 Hz, 1H), 6.01 (d, J=11.1 Hz, 1H), 5.32 (s, 1H), 4.99 (s, 1H), 4.43 (dd, J=4.3, 7.7 Hz, 1H), 4.23 (m, 1H), 3.79 (m, 1H), 3.47 (m, 1H), 3.19 (m, 1H), 2.90 (m, 1H), 2.85-2.77 (m, 2H), 2.60 (d, J=9.8 Hz, 1H), 2.32 (dd, J=6.8, 13.3 Hz, 1H), 2.23 (dd, J=7.3, 13.3 Hz, 1H), 2.01-1.21 (m, 20H), 1.41 (s, 3H), 0.87 (d, J=5.6 Hz, 3H), 0.55 (s, 3H).

Compound No. 61b:
[α]$^{24}_D$=+32.12 (c 0.57, CHCl$_3$) $^1$H NMR (CDCl$_3$) δ: 7.31-7.20 (m, 5H), 6.37 (d, J=11.1 Hz, 1H), 6.02 (d, J=11.1 Hz, 1H), 5.34 (s, 1H), 5.00 (s, 1H), 4.44 (dd, J=4.3, 7.7 Hz, 1H), 4.24 (m, 1H), 3.83 (m, 1H), 3.48 (m, 1H), 3.18 (m, 1H), 2.91 (m, 1H), 2.85-2.76 (m, 2H), 2.60 (dd, J=3.0, 13.3 Hz, 1H), 2.53 (brs, 1H), 2.32 (dd, J=7.7, 13.3 Hz, 1H), 2.02-1.20 (m, 19H), 1.69 (dd, J=5.1, 13.3 Hz, 1H), 1.49 (s, 3H), 0.96 (d, J=6.8 Hz, 3H), 0.56 (s, 3H).

Compound No. 61c:
[α]$^{24}_D$=+56.13 (c 0.16, CHCl$_3$) $^1$H NMR (CDCl$_3$) δ: 7.30-7.19 (m, 5H), 6.37 (d, J=11.5 Hz, 1H), 6.02 (d, J=11.1 Hz, 1H), 5.33 (s, 1H), 4.99 (s, 1H), 4.44 (dd, J=4.3, 7.7 Hz, 1H), 4.23 (m, 1H), 3.97 (m, 1H), 3.26 (m, 1H), 3.19 (m, 1H), 2.90 (m, 1H), 2.83 (d, J=13.3 Hz, 1H), 2.76 (m, 1H), 2.61 (d, J=13.3 Hz, 1H), 2.31 (dd, J=6.4, 13.3 Hz, 1H), 2.14 (dd, J=6.4, 12.8 Hz, 1H), 2.01-1.13 (m, 19H), 1.62 (dd, J=8.1, 12.8 Hz, 1H), 1.25 (s, 3H), 0.89 (d, J=6.0 Hz, 3H), 0.54 (s, 3H).

Compound No. 61d:
[α]$^{24}_D$=+1.81 (c 0.22, CHCl$_3$) $^1$H NMR (CDCl$_3$) δ: 7.28-7.16 (m, 5H), 6.36 (d, J=11.5 Hz, 1H), 6.01 (d, J=11.5 Hz, 1H), 5.32 (m, 1H), 4.99 (s, 1H), 4.43 (m, 1H), 4.22 (m, 1H), 3.96 (m, 1H), 3.26 (m, 1H), 3.18 (m, 1H), 2.89 (m, 1H), 2.81

(m, 1H), 2.72 (m, 1H), 2.58 (m, 1H), 2.57-2.27 (m, 2H), 2.17 (dd, J=6.4, 12.4 Hz, 1H), 2.02-1.13 (m, 18H), 1.75 (dd, J=8.1, 12.4 Hz, 1H), 1.23 (s, 3H), 0.96 (d, J=6.4 Hz, 3H), 0.55 (s, 3H).

Example 4

Production of 1α,25-dihydroxyvitamin D₃-26,23-lactam-N-(3-phenyl)propyl (Compound No. 71)

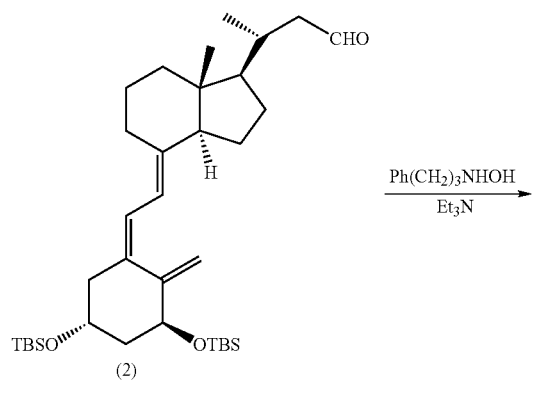

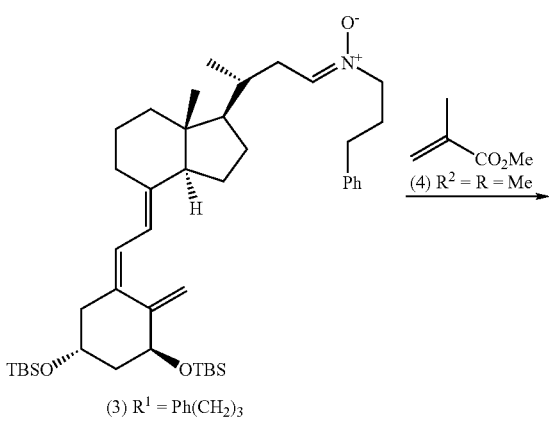

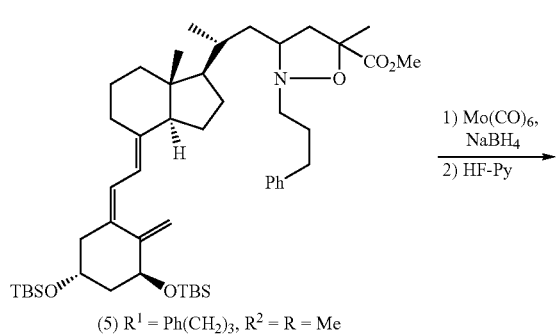

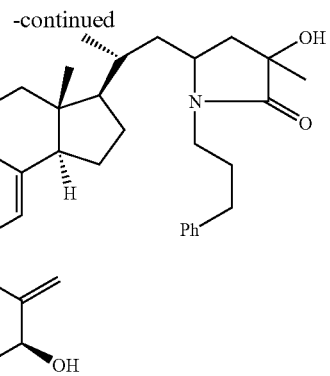

Compound 71

(1) By using Compound (2) (120.7 mg, 0.206 mmol) and 3-phenylpropylhydroxylamine (63.0 mg, 0.42 mmol) obtained in Reference Example 2, a process similar to Example 1 (1) was carried out to obtain Compound (3) (R¹=Ph(CH₂)₃) (166.0 mg, 100%) as colorless transparent oily substance.

¹H NMR (CDCl₃) δ: 7.30-7.18 (m, 5H), 6.65 (t, J 5.7 Hz, 1H), 6.24 (d, J=11.2 Hz, 1H), 6.02 (d, J=11.2 Hz, 1H), 5.18 (d, J=1.5 Hz, 1H), 4.86 (d, J=2.4 Hz, 1H), 4.37 (m, 1H), 4.21 (m, 1H), 3.77 (m, 1H), 2.87-2.81 (m, 2H), 2.68 (t, J=7.4 Hz, 2H), 2.61-2.43 (m, 3H), 2.27 (m, 2H), 2.00-1.32 (m, 14H), 1.01 (d, J=6.6 Hz, 3H), 0.88 (m, 18H), 0.56 (s, 3H), 0.07 (s, 12H).

(2) The above obtained Compound (3) (R¹=Ph(CH₂)₃) (166.0 mg, 0.23 mmol) was subjected to a process similar to Example 1(2) to obtain Compound (5) (R¹=Ph(CH₂)₃, R²=R=Me) (151.2 mg, 90%) as a colorless transparent oily substance.

¹H NMR (CDCl₃) δ: 7.30-7.14 (m), 6.24 (d, J=11.2 Hz), 6.02 (d, J=11.2 Hz), 5.19 (m), 4.87 (m), 4.38 (m), 4.20 (m), 3.76-3.72 (m), 2.85-2.44 (m), 2.24 (dd, J=7.7, 12.7 Hz), 1.97-1.26(m), 0.90-0.88 (m), 0.54-0.51 (m), 0.07 (m).

(3) The above obtained Compound (5) (R¹=Ph(CH₂)₃, R²=R=Me) (151.2 mg, 0.184 mmol) was subjected to a process similar to Example 1(3) to obtain a lactam cyclic compound (109.4 mg, 75%) as colorless transparent oily substance.

¹H NMR (CDCl₃) δ: 7.35-7.18 (m), 6.26 (d, J=11.2 Hz), 6.05 (d, J=11.2 Hz), 5.23 (s), 5.21 (s), 4.91 (s), 4.90 (s), 4.41 (m), 4.23 (m), 3.72-3.44 (m), 3.03 (m), 2.86 (d, J=12.9 Hz), 2.61 (m), 2.48 (d, J=11.5 Hz), 2.43-2.22 (m), 2.01-1.27 (m), 0.92 (m), 0.59-0.55 (m), 0.08 (m).

The obtained lactam cyclic compound (95.0 mg, 0.12 mmol) was subjected to a process similar to Example 1(3) (diastereomer isolation was performed by normal phase HPLC (silica column, moving phase: hexane/ethyl acetate/2-propanol=32/58/10 or hexane/ethyl acetate/2-propanol=19/78/3) to obtain Compound No. 71a (23S, 25S body) (14.2 mg, 21%), Compound No. 71b (23R, 25R body) (14.4 mg, 21%), Compound No. 71c (23S, 25R body) (9.2 mg, 14%) and Compound No. 71d (23R, 25S body) (7.6 mg, 11%), respectively.

Compound No. 71a:

[α]²⁴_D=+10.47 (c 0.45, CHCl₃) ¹H NMR (CDCl₃) δ: 7.28 (m, 2H), 7.19 (m, 3H), 6.37 (d, J=11.1 Hz, 1H), 6.02 (d,

J=11.1 Hz, 1H), 5.33 (s, 1H), 4.99 (s, 1H), 4.43 (dd, J=4.3, 7.7, Hz, 1H), 4.23 (m, 1H), 3.68 (m, 1H), 3.60 (m, 1H), 3.01 (m, 1H), 2.83 (d, J=12.8 Hz, 1H), 2.63 (m, 3H), 2.32 (m, 1H), 2.29 (dd, J=7.3, 13.3 Hz, 1H), 2.07-1.25 (m, 21H), 1.60 (dd, J=5.6, 13.3 Hz, 1H), 1.43 (s, 3H), 0.95 (d, J=5.6 Hz, 3H), 0.57 (s, 3H).

Compound No. 71b:

$[\alpha]^{24}_D$=+26.19 (c 0.57, CHCl$_3$) $^1$H NMR (CDCl$_3$) δ: 7.27 (m, 2H), 7.18 (m, 3H), 6.36 (d, J=11.1 Hz, 1H), 6.02 (d, J=11.5 Hz, 1H), 5.35 (s, 1H), 5.00 (s, 1H), 4.44 (m, 1H), 4.24 (m, 1H), 3.61 (m, 2H), 3.00 (m, 1H), 2.83 (m, 1H), 2.61 (m, 3H), 2.37 (dd, J=7.7, 13.3 Hz, 1H), 2.32 (dd, J=6.4, 13.3 Hz, 1H), 2.04-1.25 (m, 21H), 1.71 (dd, J=5.1, 13.3 Hz, 1H), 1.43 (s, 3H), 0.97 (d, J=6.8 Hz, 3H), 0.53 (s, 3H).

Compound No. 71c:

$[\alpha]^{24}_D$=+56.21 (c 0.65, CHCl$_3$) $^1$H NMR (CDCl$_3$) δ: 7.29 (m, 2H), 7.19 (m, 3H), 6.37 (d, J=11.1 Hz, 1H), 6.01 (d, J=11.1 Hz, 1H), 5.33 (s, 1H), 4.99 (s, 1H), 4.43 (dd, J=4.3, 7.7 Hz, 1H), 4.23 (m, 1H), 3.63 (m, 1H), 3.48 (m, 1H), 3.01 (m, 1H), 2.83 (d, J=12.8 Hz, 1H), 2.60 (m, 3H), 2.31 (dd, J=6.4, 13.3 Hz, 1H), 2.23 (m, 1H), 2.04-1.24 (m, 22H), 1.33 (s, 3H), 0.95 (d, J=6.0 Hz, 3H), 0.55 (s, 3H).

Compound No. 71d:

$[\alpha]^{24}_D$=+3.58 (c 0.24, CHCl$_3$) $^1$H NMR (CDCl$_3$) δ: 7.29 (m, 2H), 7.18 (m, 3H), 6.38 (d, J=11.1 Hz, 1H), 6.03 (d, J=11.1 Hz, 1H), 5.35 (s, 1H), 5.01 (s, 1H), 4.44 (m, 1H), 4.24 (m, 1H), 3.66 (m, 1H), 3.43 (m, 1H), 3.02 (m, 1H), 2.83 (d, J=12.8 Hz, 1H), 2.60 (m, 3H), 2.32 (dd, J=6.4, 13.3 Hz, 1H), 2.27 (dd, J=6.4, 12.8 Hz, 1H), 2.08-1.06 (m, 21H), 1.81 (dd, J=7.3, 12.8 Hz, 1H), 1.33 (s, 3H), 1.00 (d, J=6.4 Hz, 3H), 0.54 (s, 3H).

Example 5

Production of 1α,25-dihydroxyvitamin D$_3$-26,23-lactam-N-(4-phenyl) butyl (Compound No. 81)

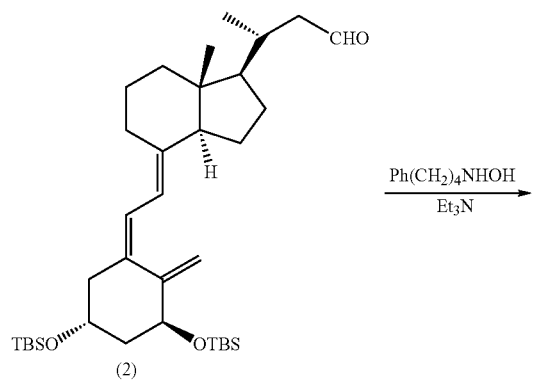

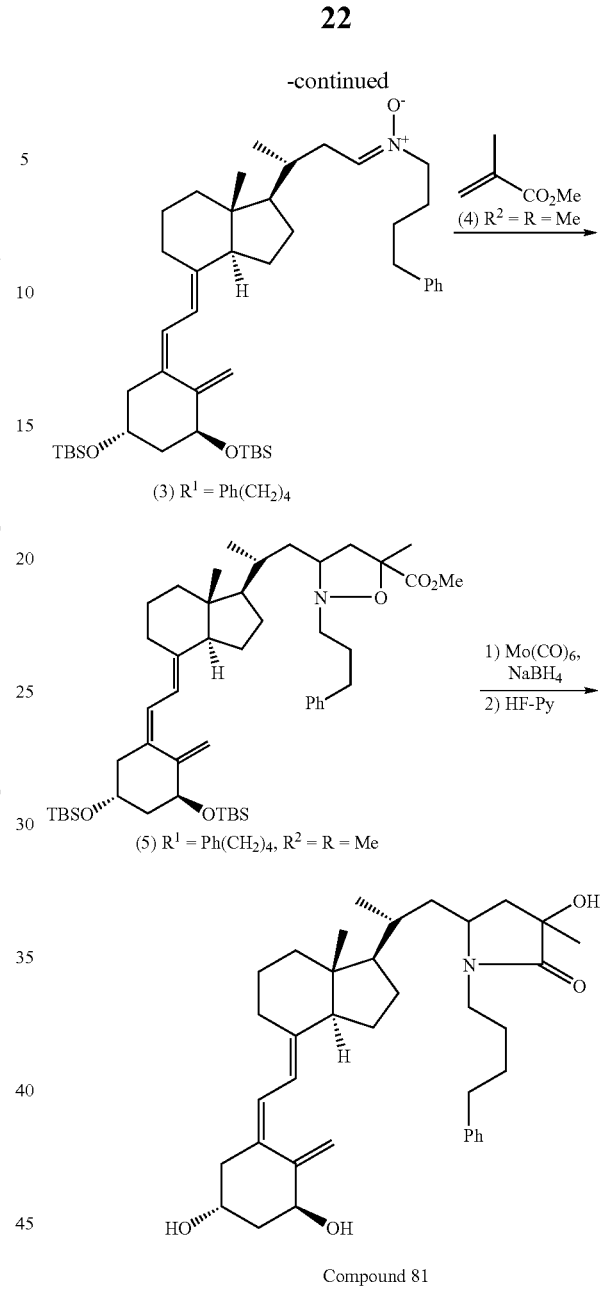

(1) By using Compound (2) (112.0 mg, 0.19 mmol) and 4-phenylbutylhydroxylamine (63.0 mg, 0.38 mmol) obtained in Reference Example 3, a process similar to Example 1 (1) was carried out to obtain Compound (3) (R$^1$=Ph(CH$_2$)$_4$) (143 mg, 100%) as colorless transparent oily substance.

$^1$H NMR (CDCl$_3$) δ: 7.29-7.15 (m, 5H), 6.66 (m, 1H), 6.23 (d, J=11.2 Hz, 1H), 6.01 (d, J=11.2 Hz, 1H), 5.18 (d, J=1.5 Hz, 1H), 4.86 (d, J=2.2 Hz, 1H), 4.37 (m, 1H), 4.19 (m, 1H), 3.76 (t, J=6.8 Hz, 2H), 2.83 (d, J=11.7 Hz, 1H), 2.66 (t, J=7.7 Hz, 2H), 2.55 (d, J=18.3 Hz, 1H), 2.45 (d, J=12.9 Hz, 1H), 2.35 (m, 1H), 2.22 (dd, J=7.8, 13.2 Hz, 1H), 1.97 (m, 2H), 1.91-1.30 (m, 14H), 1.66 (m, 2H), 0.99 (d, J=6.6 Hz, 3H), 0.89 (s, 9H), 0.88 (s, 9H), 0.55 (s, 3H), 0.06 (s, 12H).

(2) The above obtained Compound (3) (R$^1$=Ph(CH$_2$)$_4$) (143.0 mg, 0.19 mmol) was subjected to a process similar to Example 1(2) to obtain Compound (5) (R$^1$=Ph(CH$_2$)$_4$, R$^2$=R=Me) (113.8 mg, 72%) as a colorless transparent oily substance.

$^1$H NMR (CDCl$_3$) δ: 7.29-7.16 (m), 6.24 (d, J=11.0 Hz), 6.02 (d, J=11.0 Hz), 5.18 (s), 4.87 (s), 4.38 (m), 4.19 (m), 3.73 (m), 3.00-1.26 (m), 0.95-0.88 (m), 0.54 (s), 0.06 (s).

(3) The above obtained Compound (5) (R$^1$=Ph(CH$_2$)$_4$, R$^2$=R=Me) (113.8 mg, 0.14 mmol) was subjected to a process similar to Example 1(3) to obtain a lactam cyclic compound (93.6 mg, 85%) as colorless transparent oily substance.

$^1$H NMR (CDCl$_3$) δ: 7.31-7.16 (m), 6.24 (d, J=11.2 Hz), 6.03 (d, J=10.8 Hz), 5.20 (m), 4.89 (m), 4.39 (m), 4.20 (m), 3.66-2.94 (m), 2.85 (d, J=11.2 Hz), 2.67-2.61 (m), 2.46 (d, J=9.9 Hz), 2.37-1.27 (m), 0.99-0.89 (m), 0.57-0.54 (m), 0.08 (m).

The obtained lactam cyclic compound (93.6 mg, 0.12 mmol) was subjected to a process similar to Example 1(3) (diastereomer isolation was performed by normal phase HPLC (silica column, moving phase:hexane/ethyl acetate/2-propanol=30/60/10 or hexane/ethyl acetate/2-propanol=15/82/3) to obtain Compound No. 81a (23S, 25S body) (11.3 mg, 17%), Compound No. 81b (23R, 25R body) (11.5 mg, 17%), Compound No. 81c (23S, 25R body) (8.3 mg, 12%) and Compound No. 81d (23R, 25S body) (6.9 mg,. 10%), respectively.

Compound No. 81a:

[α]$^{24}_D$=+12.89 (c 0.94, CHCl$_3$) $^1$H NMR (CDCl$_3$) δ: 7.27 (m, 2H), 7.17 (m, 3H), 6.37 (d, J=11.1 Hz, 1H), 6.02 (d, J=11.5 Hz, 1H), 5.33 (s, 1H), 4.99 (s, 1H), 4.43 (m, 1H), 4.23 (m, 1H), 3.64-3.56 (m, 2H), 2.96 (m, 1H), 2.84 (d, J=12.8 Hz, 1H), 2.69-2.59 (m, 3H), 2.32 (dd, J=6.8, 14.5 Hz, 1H), 2.29 (m, 1H), 2.01-1.25 (m, 24H), 1.42 (s, 3H), 0.92 (brs, 3H), 0.57 (s, 3H).

Compound No. 81b:

[α]$^{24}_D$=+24.27 (c 1.05, CHCl$_3$) $^1$H NMR (CDCl$_3$) δ: 7.26 (m, 2H), 7.16 (m, 3H), 6.37 (d, J=11.5 Hz, 1H), 6.03 (d, J=11.5 Hz, 1H), 5.34 (s, 1H), 5.00 (s, 1H), 4.44 (m, 1H), 4.23 (m, 1H), 3.63 (m, 1H), 3.58 (m, 1H), 3.00 (m, 1H), 2.96 (m, 1H), 2.83 (d, J=12.4 Hz, 1H), 2.62 (m, 3H), 2.36 (dd, J=7.7, 13.3 Hz, 1H), 2.32 (dd, J=6.4, 13.3 Hz, 1H), 2.05-1.17 (m, 23H), 1.70 (dd, J=5.6, 13.3 Hz, 1H), 1.42 (s, 3H), 0.97 (d, J=6.4 Hz, 3H), 0.54 (s, 3H).

Compound No. 81c:

[α]$^{24}_D$=+44.34 (c 0.61, CHCl$_3$) $^1$H NMR (CDCl$_3$) δ: 7.27 (m, 2H), 7.17 (m, 3H), 6.37 (d, J=11.1 Hz, 1H), 6.02 (d, J=11.1 Hz, 1H), 5.33 (s, 1H), 4.99 (s, 1H), 4.44 (m, 1H), 4.23 (m, 1H), 3.62 (m, 1H), 3.41 (m, 1H), 2.97 (m, 1H), 2.83 (d, J=12.5 Hz, 1H), 2.70-2.57 (m, 3H), 2.31 (dd, J=6.4, 13.3 Hz, 1H), 2.22 (dd, J=6.4, 12.4 Hz, 1H), 2.01-1.20 (m, 25H), 1.68 (dd, J=7.7, 12.4 Hz, 1H), 1.33 (s, 3H), 0.91 (d, J=6.0 Hz, 3H), 0.55 (s, 3H).

Compound No. 81d:

[α]$^{24}_D$=−5.87 (c 0.41, CHCl$_3$) $^1$H NMR (CDCl$_3$) δ: 7.28 (m, 2H), 7.17 (m, 3H), 6.38 (d, J=11.5 Hz, 1H), 6.03 (d, J=11.1 Hz, 1H), 5.34 (s, 1H), 5.01 (s, 1H), 4.44 (m, 1H), 4.23 (m, 1H), 3.68 (m, 1H), 3.37 (m, 1H), 2.98 (m, 1H), 2.83 (d, J=12.8 Hz, 1H), 2.68-2.59 (m, 3H), 2.33 (m, 1H), 2.27 (dd, J=6.4, 12.4 Hz, 1H), 2.04-1.25 (m, 23H), 1.81 (dd, J=7.7, 12.4 Hz, 1H), 1.33 (s, 3H), 0.98 (d, J=6.4 Hz, 3H), 0.55 (s, 3H).

Example 6

Production of 1α,25-dihydroxyvitamin D$_3$-26,23-lactam-N-(4-methoxy) benzyl(Compound No. 101)

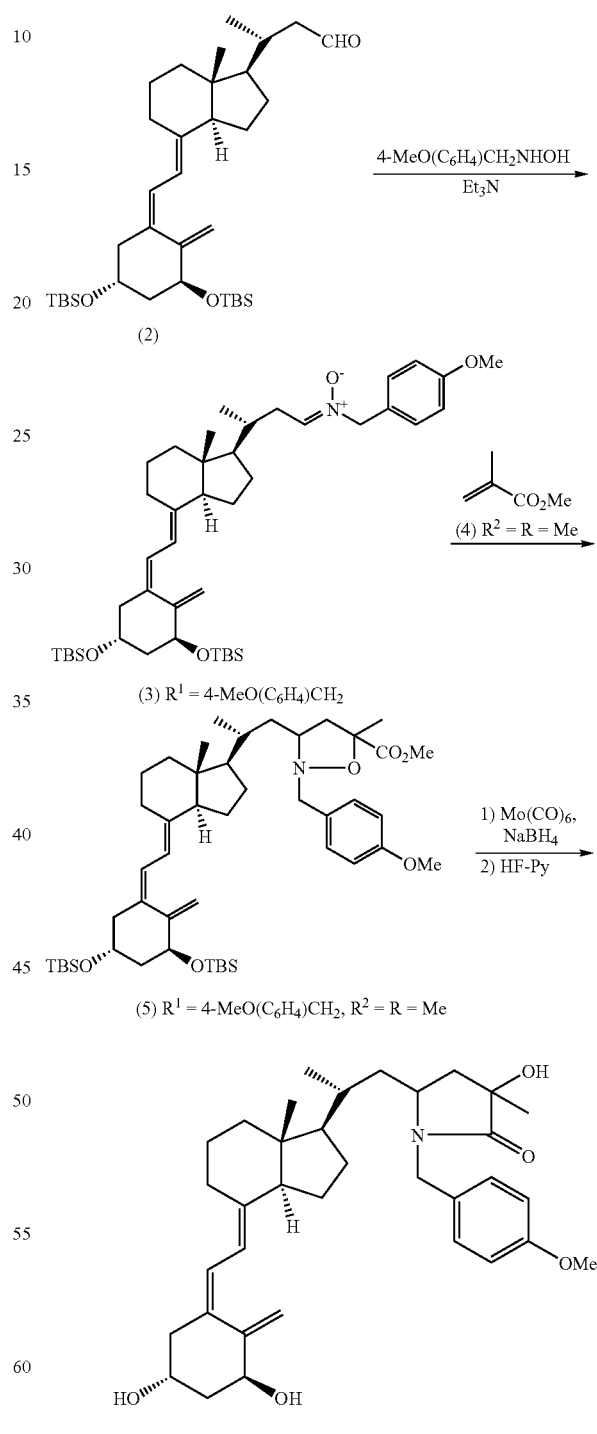

Compound 101

(1) By using Compound (2) (107.6 mg, 0.18 mmol) and 4-methoxybenzylhydroxylamine (56.0 mg, 0.37 mmol)

obtained in Reference Example 4, a process similar to Example 1 (1) was carried out to obtain Compound (3) (R$^1$=4-MeO(C$_6$H$_4$)CH$_2$) (164.6 mg, 100%) as colorless transparent oily substance.

$^1$H NMR (CDCl$_3$) δ: 7.32 (d, J=8.8 Hz, 2H), 6.91 (d, J=8.8 Hz, 2H), 6.60 (t, J=5.5 Hz, 1H), 6.22 (d, J=11.2 Hz, 1H), 6.00 (d, J=11.2 Hz, 1H), 5.17 (d, J=1.7 Hz, 1H), 4.85 (s, 1H), 4.36 (dd, J=3.4, 6.6 Hz, 1H), 4.19 (m, 1H), 3.81 (m, 3H), 2.82 (d, J=12.0 Hz, 1H), 2.55 (d, J=17.1 Hz, 1H), 2.44 (d, J=13.1 Hz, 1H), 2.35 (m, 1H), 2.22 (dd, J=7.6, 13.1 Hz, 1H), 1.98-1.28 (m, 16H), 0.92 (d, J=6.6 Hz, 3H), 0.87 (s, 18H), 0.52 (s, 3H), 0.06 (m, 12H).

(2) The above obtained Compound (3) (R$^1$=4-MeO(C$_6$H$_4$)CH$_2$) (164.6 mg, 0.23 mmol) was subjected to a process similar to Example 1(2) to obtain Compound (5) (R$^1$=4-MeO(C$_6$H$_4$)CH$_2$, R$^2$=R=Me) (103.0 mg, 68%) as a colorless transparent oily substance.

$^1$H NMR (CDCl$_3$) δ: 7.35-7.28 (m), 6.86-6.82 (m), 6.23 (d, J=11.0 Hz), 6.01 (d, J=11.0 Hz), 5.18 (s), 4.86 (s), 4.37 (dd, J=3.2, 6.3 Hz), 4.19 (m), 4.13-3.87 (m), 3.80-3.76 (m), 3.13-2.89 (m), 2.82 (d, J=12.4 Hz), 2.61-1.19 (m), 2.45 (d, J=13.4 Hz), 0.91-0.88 (m), 0.54-0.50 (m), 0.07 (m).

(3) The above obtained Compound (5) (R$^1$=4-MeO(C$_6$H$_4$)CH$_2$, R$^2$=R=Me) (103.0 mg, 0.13 mmol) was subjected to a process similar to Example 1(3) to obtain a lactam cyclic compound (65.9 mg, 66%) as colorless transparent oily substance.

$^1$H NMR (CDCl$_3$) δ: 7.17-7.08 (m), 6.84 (d, J=8.5 Hz), 6.23 (d, J=11.2 Hz), 6.02 (d, J=11.2 Hz), 5.19 (s), 4.98-4.87 (m), 4.38 (m), 4.20 (m), 4.01-3.86 (m), 3.81-3.79 (m), 3.51 (m), 3.26 (m), 2.82 (d, J=12.7 Hz), 2.45 (d, J=12.9 Hz), 2.35-1.27 (m), 0.90-0.89 (m), 0.54-0.50 (m), 0.08 (m).

The obtained lactam cyclic compound (65.9 mg, 0.083 mmol) was subjected to a process similar to Example 1(3) (diastereomer isolation was performed by normal phase HPLC (silica column, moving phase: hexane/ethyl acetate/2-propanol=35/52/13 or hexane/ethyl acetate/2-propanol=15/82/3) to obtain Compound No. 101a (23S, 25S body) (8.2 mg, 17%), Compound No. 101b (23R, 25R body) (11.9 mg, 25%), Compound No. 101c (23S, 25R body) (6.4 mg, 14%) and Compound No. 101d (23R, 25S body) (6.6 mg, 14%), respectively.

Compound No. 101a:
[α]$^{24}_D$=−11.68 (c 0.68, CHCl$_3$) $^1$H NMR (CDCl$_3$) δ: 7.15 (d, J=8.6 Hz, 2H), 6.84 (d, J=8.6 Hz, 2H), 6.36 (d, J=11.1 Hz, 1H), 6.01 (d, J=11.1 Hz, 1H), 5.32 (s, 1H), 4.99 (s, 1H), 4.92 (d, J=15.0 Hz, 1H), 4.43 (m, 1H), 4.23 (m, 1H), 3.90 (d, J=15.0 Hz, 1H), 3.79 (s, 3H), 3.48 (m, 1H), 2.82 (d, J=12.4 Hz, 1H), 2.59 (d, J=13.7 Hz, 1H), 2.32 (m, 1H), 2.25 (dd, J=7.7, 13.3 Hz, 1H), 2.08-1.25 (m, 15H), 1.48 (s, 3H), 0.89-0.84 (m, 5H), 0.79 (d, J=6.4 Hz, 3H), 0.53 (s, 3H).

Compound No. 101b:
[α]$^{24}_D$=+17.00 (c 1.10, CHCl$_3$) $^1$H NMR (CDCl$_3$) δ: 7.12 (d, J=8.6 Hz, 2H), 6.85 (d, J=8.6 Hz, 2H), 6.36 (d, J=11.1 Hz, 1H), 6.01 (d, J=11.1 Hz, 1H), 5.33 (s, 1H), 5.00 (s, 1H), 4.93 (d, J=15.0 Hz, 1H), 4.44 (dd, J=4.3, 7.7 Hz, 1H), 4.23 (m, 1H), 3.97 (d, J=15.4 Hz, 1H), 3.79 (s, 3H), 3.47 (m, 1H), 2.82 (d, J=12.4 Hz, 1H), 2.59 (d, J=13.3 Hz, 1H), 2.34 (dd, J=8.1, 13.7 Hz, 1H), 2.32 (dd, J=6.4, 12.8 Hz, 1H), 2.08-1.89 (m, 5H), 1.76 (dd, J=5.1, 13.3 Hz, 1H), 1.69-0.99 (m, 14H), 1.49 (s, 3H), 0.87 (d, J=6.9 Hz, 3H), 0.50 (s, 3H).

Compound No. 101c:
[α]$^{24}_D$=+15.58 (c 0.46, CHCl$_3$) $^1$H NMR (CDCl$_3$) δ: 7.11 (d, J=8.6 Hz, 2H), 6.84 (d, J=8.6 Hz, 2H), 6.36 (d, J=11.1 Hz, 1H), 6.01 (d, J=11.1 Hz, 1H), 5.33 (s, 1H), 4.99 (s, 1H), 4.94 (d, J=14.5 Hz, 1H), 4.43 (dd, J=4.3, 7.7 Hz, 1H), 4.23 (m, 1H), 3.90 (d, J=15.0 Hz, 1H), 3.79 (s, 3H), 3.26 (m, 1H), 2.82 (d, J=12.4 Hz, 1H), 2.59 (dd, J=3.0, 13.7 Hz, 1H), 2.31 (m, 1H), 2.19 (dd, J=6.4, 12.8 Hz, 1H), 2.02-1.14 (m, 20H), 1.71 (dd, J=7.8, 12.8 Hz, 1H), 1.33 (s, 3H), 0.88 (m, 1H), 0.78 (d, J=6.4 Hz, 3H), 0.52 (s, 3H).

Compound No. 101d:
[α]$^{24}_D$=+3.49 (c 0.53, CHCl$_3$) $^1$H NMR (CDCl$_3$) δ: 7.08 (d, J=8.6 Hz, 2H), 6.85 (d, J=8.6 Hz, 2H), 6.36 (d, J=11.1 Hz, 1H), 6.01 (d, J=11.1 Hz, 1H), 5.33 (s, 1H), 4.99 (s, 1H), 4.95 (d, J=15.0 Hz, 1H), 4.44 (m 1H), 4.22 (m, 1H), 3.98 (d, J=15.0 Hz, 1H), 3.80 (s, 3H), 3.25 (m, 1H), 2.82 (d, J=12.4 Hz, 1H), 2.59 (d, J=14.1 Hz, 1H), 2.32 (m, 1H), 2.24 (dd, J=6.4, 12.4 Hz, 1H), 2.13-1.22 (m, 21H), 1.86 (dd, J=7.7, 12.4 Hz, 1H), 1.36 (s, 3H), 1.09 (m, 2H), 0.88 (d, J=6.5 Hz, 3H), 0.50 (s, 3H).

Example 7

Production of 1α,25-dihydroxyvitamin D$_3$-27-homo-26,23-lactam-N-(2-phenethyl) (Compound No. 62)

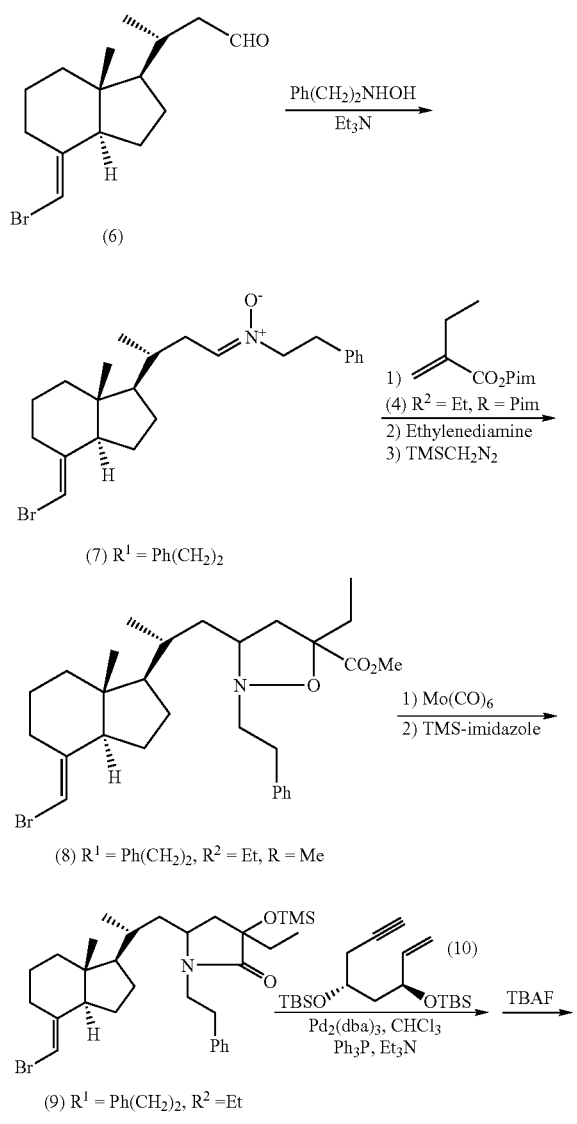

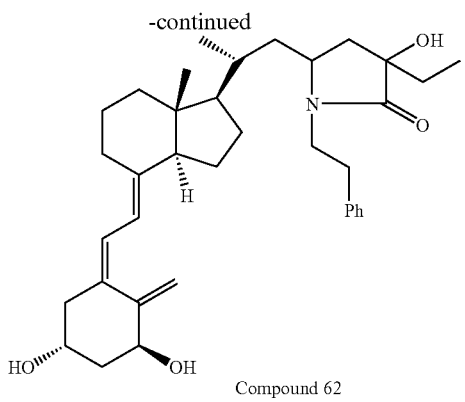

Compound 62

(1) By using Compound (5) (788.2 mg, 2.64 mmol) obtained according to a method described in literature (for example, the description of International Publication WO95/33716) and 2-phenethylhydroxylamine (722.0 mg, 5.26 mmol) obtained in Reference Example 1, a process similar to Example 1 (1) was carried out to obtain Compound (7) ($R^1$=Ph($CH_2$)$_2$) (1.28 g, 100%) as colorless transparent oily substance.

$^1$H-NMR (CDCl$_3$) δ: 7.31-7.20 (m, 5H), 6.38 (t, J=5.7 Hz, 1H), 5.64 (s, 1H), 3.97 (t, J=6.7 Hz, 2H), 3.23-3.19 (m, 2H), 2.88-2.86 (m, 1H), 2.46 (dt, J=17.2, 4.4 Hz, 1H), 2.28-2.19 (m, 1H), 1.97-1.13 (m, 12H), 0.79 (d, J=6.6 Hz, 3H), 0.53 (s, 3H).

(2) Above-obtained Compound (7) ($R^1$=Ph($CH_2$)$_2$) (577.0 mg, 1.43 mmol) was dissolved in anhydrous toluene (10.0 mL). To the solution was added an anhydrous toluene solution (5.0 mL) of Compound (4) ($R^2$=Et, R=Pim (phthalimidemethyl)) (463.1 mg, 1.79 mmol) obtained in Reference Example 5, and the resulting mixture was stirred for 12 hr at 90° C. under nitrogen atmosphere. The reaction mixture was concentrated in vacuo, and the obtained residue was roughly purified by silica gel chromatography (n-hexane:ethyl acetate=4:1). The obtained compound was dissolved in n-butanol (25.0 mL), ethylenediamine (3.3 mL) was added, and the mixture was stirred for 1 hr at 90° C. The reaction mixture was concentrated in vacuo after the addition of water (30 mL). The obtained residue was diluted with ethyl acetate and washed with 1M hydrochloric acid, and the organic layer was dried over magnesium sulfate and concentrated in vacuo. The obtained residue was roughly purified by silica gel chromatography (n-hexane:ethyl acetate=4:1). The product was dissolved in a mixed solvent of benzene (4.5 mL) and methanol (0.5 mL), trimethylsilyldiazomethane (1.0 mL, 0.59 mmol) was added to the solution, and the mixture was stirred for 15 min at room temperature. The reaction mixture was concentrated in vacuo to obtain Compound (8) ($R^1$=Ph($CH_2$)$_2$, $R^2$=Et, R=Me) (269.1 mg, 41%).

$^1$H-NMR (CDCl$_3$) δ: 7.32-7.15 (m, 5H), 5.64 (brs, 1H), 3.79-3.75 (m, 3H), 3.10-0.72 (m, 30H), 0.57-0.52 (m, 3H).

(3) The above obtained Compound (8) ($R^1$=Ph($CH_2$)$_2$, $R^2$=Et, R=Me) (269.1 mg, 0.50 mmol) was dissolved in a mixed solvent of acetonitrile (7.0 mL) and water (1.0 mL), molybdenum hexacarbonyl (205.0 mg, 0.78 mmol) was added to the solution, and the mixture was stirred for 12 hr at 90° C. The reaction mixture was filtered through celite, and the distillate was concentrated in vacuo. The obtained residue was purified by silica gel column chromatography (n-hexane: ethyl acetate=2:1) to obtain a lactam cyclic compound (132.2 mg, 53%).

$^1$H-NMR (CDCl$_3$) δ: 7.33-7.16 (m, 5H), 5.66 (brs, 1H), 3.85-3.73 (m, 1H), 3.55-3.46 (m, 1H), 3.32-3.16 (m, 1H), 2.94-2.64 (m, 3H), 2.28-0.82 (m, 24H), 0.61-0.56 (m, 3H).

The obtained lactam cyclic compound (132.2 mg, 0.26 mmol) was dissolved in anhydrous dichloromethane (5.0 mL), trimethylsilylimidazole (0.2 mL, 1.30 mmol) was added to the solution, and the mixture was stirred for 12 hr at room temperature under nitrogen atmosphere. After the addition of water at 0° C., the reaction mixture was further stirred, and then it was extracted with dichloromethane. The organic layer was dried over magnesium sulfate and concentrated in vacuo, and the obtained residue was purified by silica gel thin layer chromatography (n-hexane:ethyl acetate=5:1) to obtain Compound (9) ($R^1$=Ph($CH_2$)$_2$, $R^2$=Et) (133.3 mg, 89%).

$^1$H-NMR (CDCl$_3$) δ: 7.33-7.16 (m, 5H), 5.68-5.64 (m, 1H), 3.77-3.50 (m, 2H), 3.28-3.10 (m, 1H), 2.92-2.75 (m, 3H), 2.23-0.75 (m, 24H), 0.58 (d, J=4.6 Hz, 3H), 0.16-0.10 (m, 9H).

(4) Triphenylphosphine (37.0 mg, 0.14 mmol) and tris (dibenzylideneacetone)dipalladium (o)-chloroform adduct (22.0 mg, 0.021 mmol) were dissolved in a mixed solvent of anhydrous toluene (1.8 mL) and triethylamine (1.8 mL), and the solution was stirred for 10 min at room temperature. To the reaction mixture was added an anhydrous toluene solution (1.8 mL) of the above obtained Compound (9) ($R^1$=Ph($CH_2$)$_2$, $R^2$=Et) (67.0 mg, 0.12 mmol) and Compound (10) (52.0 mg, 0.14 mmol) synthesized according to a method of Trost et al. (Tetrahedron Lett., vol. 35, issue 44, 8119-8122 (1994)), and the mixture was stirred for 2 hr at 120° C. under argon atmosphere. The reaction mixture was washed with ethyl acetate after the addition of saturated ammonium chloride solution. The aqueous phase was made weakly basic by adding saturated sodium bicarbonate solution, and then extracted with ethyl acetate. The combined organic layers were washed with brine and dried over magnesium sulfate. The residue obtained by concentration in vacuo was roughly purified by silica gel thin layer chromatography (n-hexane:ethyl acetate=5:1). The obtained residue (92.5 mg) was dissolved in anhydrous tetrahydrofuran (3.0 mL), a tetrahydrofuran solution (0.44 mL, 1M) of tetrabutylammonium fluoride (0.44 mmol) was added, and the mixture was stirred for 2 hr at 50° C. under nitrogen atmosphere. The reaction mixture was extracted with ethyl acetate after the addition of saturated ammonium chloride solution. The organic layer was washed with brine, dried over magnesium sulfate and concentrated in vacuo. The residue was purified by silica gel thin layer chromatography (n-hexane:acetone=1:1) to obtain Compound No. 62 (22.5 mg). The obtained Compound No. 62 was purified by normal phase HPLC (CHIRALPAK AD column, moving phase: 30% ethanol/n-hexane) and reverse phase HPLC (ODS column, moving phase: A=95% $H_2$O/$CH_3$CN; B=$CH_3$CN/MeOH=6/4 (0.5% $H_2$O); B=70%) and normal phase HPLC (CHIRALPAK AD column, moving phase: 15% ethanol/n-hexane) to obtain Compound No. 62a (23S, 25S body) (1.2 mg, 2%), Compound No. 62b (23R, 25R body) (2.2 mg, 3%) and Compound No. 62d (23R, 25S body)(0.6 mg, 1%), respectively.

Compound No. 62a:

$^1$H-NMR (CDCl$_3$) δ: 7.33-7.18 (m, 5H), 6.38 (d, J=11.5 Hz, 1H), 6.02 (d, J=11.0 Hz, 1H), 5.33 (s, 1H), 5.00 (s, 1H), 4.43 (brs, 1H), 4.23 (brs, 1H), 3.80-3.70 (m, 1H), 3.55-3.45 (m, 1H), 3.25-3.15 (m, 1H), 2.93-2.75 (m, 3H), 2.63-2.55 (m, 1H), 2.32 (dd, J=13.7, 6.7 Hz, 1H), 2.11 (dd, J=13.7, 7.3 Hz, 1H), 2.04-1.10 (m, 19H), 0.96 (t, J=7.4 Hz, 3H), 0.88 (d, J=5.6 Hz, 3H), 0.56 (s, 3H).

Compound No. 62b:

$^1$H-NMR (CDCl$_3$) δ: 7.34-7.19 (m, 5H), 6.38 (d, J=11.2 Hz, 1H), 6.03 (d, J=11.2 Hz, 1H), 5.34 (s, 1H), 5.01 (s, 1H), 4.44 (brs, 1H), 4.25 (brs, 1H), 3.85-3.77 (m, 1H), 3.55-3.47 (m, 1H), 3.25-3.15 (m, 1H), 2.95-2.74 (m, 3H), 2.61 (dd, J=13.7, 3.4 Hz, 1H), 2.32 (dd, J=13.4, 6.7 Hz, 1H), 2.20 (dd, J=13.5, 7.7 Hz, 1H), 2.12-1.15 (m, 19H), 1.05-0.91 (m, 6H), 0.56 (s, 3H).

Compound No. 62d:

$^1$H-NMR (CDCl$_3$) δ: 7.32-7.16 (m, 5H), 6.38 (d, J=11.0 Hz, 1H), 6.03 (d, J=11.2 Hz, 1H), 5.34 (s, 1H), 5.01 (s, 1H), 4.44 (brs, 1H), 4.24 (brs, 1H), 4.06-3.95 (m, 1H), 3.35-3.27 (m, 1H), 3.24-3.14 (m, 1H), 2.95-2.69 (m, 3H), 2.64-2.57 (m, 1H), 2.42 (s, 1H), 2.36-2.23 (m, 2H), 2.04-1.06 (m, 18H), 1.00 (d, J=6.3 Hz, 3H), 0.85 (t, J=7.4 Hz, 3H), 0.58 (s, 3H).

Example 8

Production of 1α,25-dihydroxyvitamin D$_3$-27-bishomo-26,23-lactam-N-(2-phenethyl) (Compound No. 63)

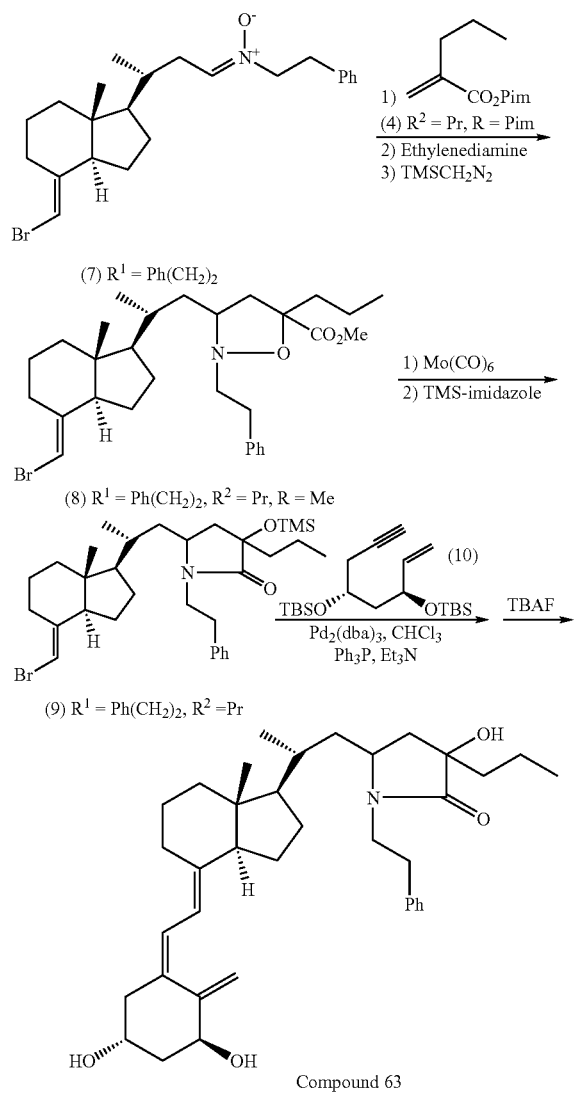

Compound 63

(1) By using Compound (7) (700.0 mg, 1.74 mmol) obtained in Example 7 and Compound (4) (R$^2$=Pr, R=Pim (phthalimidemethyl) (643.2 mg, 2.35 mmol) obtained in Reference Example 6, a process similar to Example 7(2) was carried out to obtain Compound (8) (R$^1$=Ph(CH$_2$)$_2$, R$^2$=Pr, R=Me) (269.0 mg, 34%).

$^1$H-NMR (CDCl$_3$) δ: 7.32-7.16 (m, 5H), 5.64 (brs, 1H), 3.78-3.74 (m, 3H), 3.10-0.80 (m, 32H), 0.57-0.51 (m, 3H).

(2) By using the above obtained Compound (8) (R$^1$=Ph(CH$_2$)$_2$, R$^2$=Pr, R=Me) (307.3 mg, 0.56 mmol), a process similar to Example 7(3) was carried out to obtain a lactam cyclic compound (170.6 mg, 59%).

$^1$H-NMR (CDCl$_3$) δ: 7.33-7.17 (m, 5H), 5.66 (brs, 1H), 3.84-3.72 (m, 1H), 3.55-3.47 (m, 1H), 3.25-3.15 (m, 1H), 2.95-2.73 (m, 3H), 2.29-0.83 (m, 26H), 0.60-0.55 (m, 3H).

By using the obtained lactam cyclic compound (170.6 mg, 0.33 mmol), a process similar to Example 6(3) was carried out to obtain Compound (9) (R$^1$=Ph(CH$_2$)$_2$, R$^2$=Pr) (73.8 mg, 90%).

$^1$H-NMR (CDCl$_3$) δ: 7.33-7.17 (m, 5H), 5.68-5.64 (m, 1H), 3.76-3.52 (m, 2H), 3.26-3.10 (m, 1H), 2.92-2.73 (m, 3H), 2.23-0.86 (m, 26H), 0.58 (d, J=5.1 Hz, 3H), 0.15-0.11 (m, 9H).

(3) By using the above obtained Compound (9) (R$^1$=Ph(CH$_2$)$_2$, R$^2$=Pr) (86.9 mg, 0.15 mmol), a process similar to Example 7(4) was carried out to obtain Compound No. 63 (29.0 mg). This compound was purified by reverse phase HPLC (ODS column, moving phase: A=95% H$_2$O/CH$_3$CN; B=CH$_3$CN/MeOH=6/4 (0.5% H$_2$O); B=70%) and normal phase HPLC (CHIRALPAK AD column, moving phase: 30% ethanol/n-hexane) to obtain Compound No. 63a (23S, 25S body) (4.5 mg, 5%), Compound No. 63b (23R, 25R body) (5.1 mg, 6%), Compound No. 63c (23S, 25R body) (1.6 mg, 2%) and Compound No. 63d (23R, 25S body) (2.7 mg, 3%), respectively.

Compound No. 63a:

$^1$H-NMR (CDCl$_3$) δ: 7.33-7.18 (m, 5H), 6.38 (d, J=11.0 Hz, 1H), 6.02 (d, J=11.2 Hz, 1H), 5.33 (s, 1H), 5.00 (s, 1H), 4.43 (brs, 1H), 4.23 (brs, 1H), 3.81-3.70 (m, 1H), 3.55-3.45 (m, 1H), 3.25-3.16 (m, 1H), 2.93-2.75 (m, 3H), 2.63-2.56 (m, 1H), 2.32 (dd, J=13.4, 6.6 Hz, 1H), 2.20-1.10 (m, 22H), 0.96 (t, J=7.0 Hz, 3H), 0.88 (d, J=5.6 Hz, 3H), 0.56 (s, 3H).

Compound No. 63b:

$^1$H-NMR (CDCl$_3$) δ: 7.34-7.19 (m, 5H), 6.38 (d, J=11.2 Hz, 1H), 6.03 (d, J=11.2 Hz, 1H), 5.34 (s, 1H), 5.01 (s, 1H), 4.44 (brs, 1H), 4.24 (brs, 1H), 3.85-3.75 (m, 1H), 3.54-3.46 (m, 1H), 3.25-3.14 (m, 1H), 2.94-2.72 (m, 3H), 2.61 (dd, J=13.5, 3.3 Hz, 1H), 2.32 (dd, J=13.4, 6.7 Hz, 1H), 2.25-2.15 (m, 2H), 2.06-1.11 (m, 20H), 1.00-0.93 (m, 6H), 0.56 (s, 3H).

Compound No. 63c:

$^1$H-NMR (CDCl$_3$) δ: 7.32-7.17 (m, 5H), 6.37 (d, J=11.2 Hz, 1H), 6.01 (d, J=11.5 Hz, 1H), 5.33 (s, 1H), 5.00 (s, 1H), 4.43 (brs, 1H), 4.23 (brs, 1H), 4.06-3.96 (m, 1H), 3.33-3.25 (m, 1H), 3.22-3.13 (m, 1H), 2.93-2.70 (m, 3H), 2.64-2.56 (m, 1H), 2.49 (s, 1H), 2.32 (dd, J=13.3, 7.0 Hz, 1H), 2.21 (dd, J=13.1, 6.4 Hz, 1H), 2.04-1.10 (m, 19H), 0.91 (d, J=6.3 Hz, 3H), 0.86 (t, J=7.0 Hz, 3H), 0.55 (s, 3H).

Compound No. 63d:

$^1$H-NMR (CDCl$_3$) δ: 7.31-7.15 (m, 5H), 6.38 (d, J=11.0 Hz, 1H), 6.03 (d, J=11.2 Hz, 1H), 5.34 (s, 1H), 5.01 (s, 1H), 4.44 (brs, 1H), 4.24 (brs, 1H), 4.07-3.97 (m, 1H), 3.35-3.28 (m, 1H), 3.23-3.14 (m, 1H), 2.95-2.69 (m, 3H), 2.64-2.57 (m, 1H), 2.49 (s, 1H), 2.36-2.23 (m, 2H), 2.06-1.05 (m, 19H), 1.00 (d, J=6.6 Hz, 3H), 0.87 (t, J=7.0 Hz, 3H), 0.58 (s, 3H).

Example 9

Production of 1α,25-dihydroxyvitamin D₃-27-phenyl-26,23-lactam-N-(2-phenethyl) (Compound No. 64)

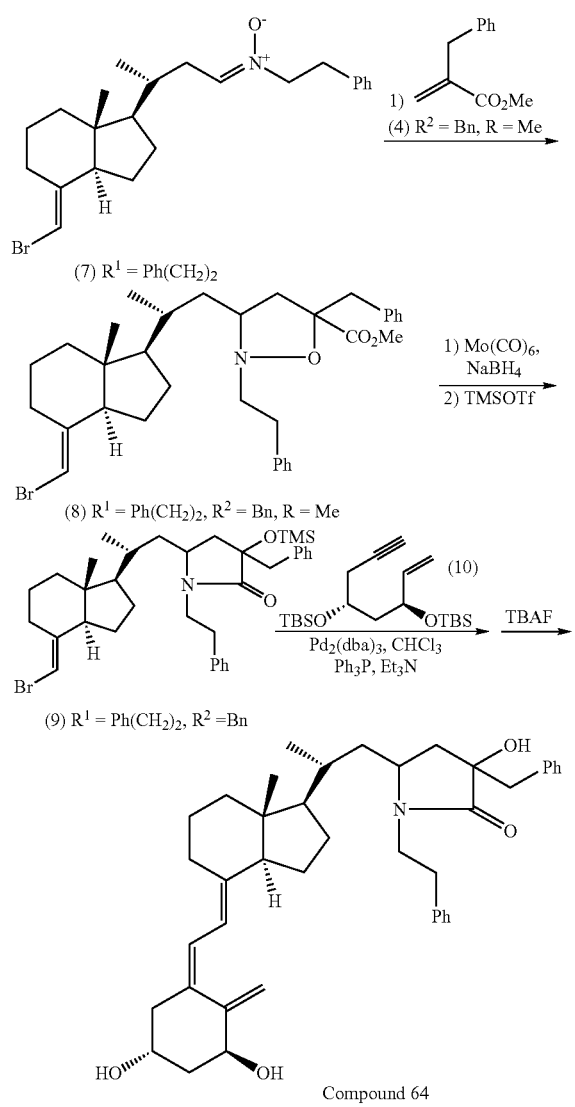

Compound 64

(1) Compound (7) (239.7 mg, 0.93 mmol) obtained in Example 7 was dissolved in dehydrated toluene (5.0 mL), Compound (4) (R²=Bn, R=Me) (530 mg, 3.0 mmol) synthesized according to a method of Basavaiah et al. (Tetrahedron Lett. Vol. 42, 477-479 (2001)) was added to the solution, and the mixture was stirred for 12 hr at 60° C. under nitrogen atmosphere and further for 2 hr at 90° C. The reaction mixture was concentrated in vacuo, and the obtained residue was purified by silica gel column chromatography (n-hexane:ethyl acetate=20:1) to obtain a crude body of Compound (8) (R¹=Ph(CH₂)₂, R²=Bn, R=Me).

(2) The obtained crude body of Compound (8) (R¹=Ph(CH₂)₂, R²=Bn, R=Me) was dissolved in a mixed solvent of acetonitrile (10.5 mL) and water (1.5 mL), molybdenum-hexacarbonyl (240 mg, 0.91 mmol) was added to the solution, and the mixture was stirred for 12 hr at 90° C. The reaction mixture was filtered through celite, and the filtrate was concentrated in vacuo. The obtained residue was purified by silica gel column chromatography (n-hexane:ethyl acetate=2:1) to obtain a lactam cyclic compound (178.1 mg, 52%).

¹H-NMR (CDCl₃) δ: 7.31-7.18 (m, 10H), 5.65 (s, 1H), 3.80-3.68 (m, 1H), 3.44-3.43 (m, 1H), 3.20-3.16 (m, 1H), 3.05-2.73 (m, 5H), 2.17-1.00 (m, 16H), 0.86-0.82 (m, 3H), 0.54-0.50 (m, 3H).

The obtained lactam cyclic compound (178.1 mg, 0.315 mmol) was dissolved in dehydrated dichloromethane (3.5 mL), 2,6-lutidine (55 μg L, 0.473 mmol) and trimethylsilyl trifluoromethanesulfonate (70 μL, 0.388 mmol) were added at 0° C. under nitrogen atmosphere, and the mixture was stirred for 1 hr at the same temperature. To the reaction mixture was added saturated sodium bicarbonate solution, and the mixture was extracted with dichloromethane after stirring. The organic layer was dried over magnesium sulfate and concentrated in vacuo. The obtained residue was purified by silica gel chromatography (n-hexane:ethyl acetate=20:1) to obtain Compound (9) (R¹=Ph(CH₂)₂, R²=Bn) (189.9 mg, 95%).

¹H-NMR (CDCl₃) δ: 7.33-7.15 (m, 10H), 5.65 (brs, 1H), 3.75-3.44 (m, 2H), 3.30-3.18 (m, 1H), 3.14-2.54 (m, 5H), 2.12-1.02 (m, 16H), 0.94-0.82 (m, 3H), 0.55-0.43 (m, 3H), 0.26-0.15 (m, 9H).

(3) By using the above obtained Compound (9) (R¹=Ph(CH₂)₂, R²=Bn) (99.1 mg, 0.16 mmol), a process similar to Example 6(4) was carried out to obtain Compound No. 64 (28.4 mg). This compound was purified by normal phase HPLC (CHIRALPAK AD column, moving phase: 20% ethanol/n-hexane) and reverse phase HPLC (ODS column, moving phase: A=95% H₂O/CH₃CN; B=CH₃CN/MeOH=6/4 (0.5% H₂O); B=75%) to obtain Compound No. 64a (23S, 25S body) (3.0 mg, 4%) and Compound No. 64b (23R, 25R body) (4.4 mg, 5%), respectively.

Compound No. 64a:
¹H-NMR (CDCl₃) δ: 7.32-7.17 (m, 10H), 6.38 (d, J=11.2 Hz, 1H), 6.02 (d, J=11.2 Hz, 1H), 5.35 (s, 1H), 5.01 (s, 1H), 4.44 (brs, 1H), 4.24 (brs, 1H), 3.76-3.66 (m, 1H), 3.50-3.40 (m, 1H), 3.24-3.16 (m, 1H), 3.05-2.58 (m, 6H), 2.38-1.12 (m, 19H), 0.80 (d, J=5.1 Hz, 3H), 0.51 (s, 3H).

Compound No. 64b:
¹H-NMR (CDCl₃) δ: 7.32-7.18 (m, 10H), 6.37 (d, J=11.2 Hz, 1H), 6.01 (d, J=11.0 Hz, 1H), 5.34 (s, 1H), 5.00 (s, 1H), 4.44 (brs, 1H), 4.23 (brs, 1H), 3.80-3.69 (m, 1H), 3.50-3.40 (m, 1H), 3.23-3.12 (m, 1H), 3.05-2.70 (m, 5H), 2.64-2.55 (m, 1H), 2.45 (s, 1H), 2.36-2.27 (m, 1H), 2.15-1.05 (m, 17H), 0.84 (d, J=6.6 Hz, 3H), 0.51 (s, 3H).

Example 10

Binding Affinity to Chick Mucosal Cell 1α,25-dihydroxyvitamin D₃ Receptor (VDR)

This receptor binding assay was performed as described by Ishizuka, et al. (Steroids, 37, 33-34 (1982)). That is, an ethanol solution (10 μl) of [26, 27-methyl-³H] 1α,25-dihydroxyvitamin D₃ (15,000 dpm, 180 Ci/mmol) and an ethanol solution (40 μl) of a compound of the present invention were charged to a 12×75 mm polypropylene tube. Chick intestinal mucosal cell 1α,25-dihydroxyvitamin D₃ receptor protein (0.2 mg) and gelatin (1 mg) were dissolved in 1 ml of phosphate buffer (pH 7.4), the solution was added to the tube, and the mixture was allowed to react for 1 hr at 25° C. One ml of a 40% polyethylene glycol 6000 solution was added to the tube, mixed vigorously, and then centrifuged (2,260×g) for 60 min at 4° C. The bottom of the tube containing the pellet was cut off into a scintillation solution vial, 10 ml of dioxane-based scintillation fluid was added, and then radioactivity was measured by a liquid scintillation counter. Regarding compounds of the present invention, the concentration at which the binding of [26, 27-methyl-$^3$H] 1α,25-dihydroxyvitamin $D_3$ to the receptor was inhibited by 50% was determined from measured values. The concentration was expressed in terms of relative strength calculated by taking the 50%-inhibition concentration of 1α,25-dihydroxyvitamin $D_3$ as 1. The results are shown in the following table.

Binding Affinity of Compounds of the Present
Invention to Chick Mucosal Cell
1α,25-Dihydroxyvitamin $D_3$ Receptor

| VDR affinity(*) | Compound No. |
|---|---|
| 1 to 1/30 | 61a, 62a, 81a |
| 1/30 to 1/100 | 11a, 51a, 63a, 64b, 101a |
| 1/100 to 1/300 | 61b, 61c, 62b, 63b, 64a, 71a |

(*)1a, 25-dihydroxyvitamin $D_3$= 1

This result shows that compounds of the present invention have very strong binding affinities to VDR. Consequently, considering the below-mentioned antagonist activities of compounds of the present invention, these compounds can be expected to have high antagonist activities to vitamin $D_3$, and it is shown that they are effective as treating agent for Paget's disease of bone, hypercalcemia and osteoporosis.

Example 11

Vitamin $D_3$ Antagonist Effect Expressed by the
Parameter of Differentiation Induction Effect on
HL-60 Cell Caused by 1 α,25-Dihydroxyvitamin $D_3$ (1) HL-60 cell line which had been purchased from a cell bank (Japanese Cancer Research Resource Bank, Cell No: JCRB0085) was used. The cell line was stored as a frozen storage stock to prevent cell characteristic changes attributable to successive cultivations. Prior to the initiation of experiments, the cells were defrosted and successive culturing was stared. For the experiments, cells whose successive culturing was from one month to about a half year were used. The successive culturing was carried out by centrifugally collecting cells which were in the state of suspension culture, and diluting the collected cell concentrate with a fresh culture medium at a ratio of about 1/100 (1-2×10$^4$ cells/ml). As the culture medium, an RPMI-1640 medium containing 10% fetal bovine serum was used.

(2) The cells which were under successive culturing in the above process (1) were centrifugally collected, and they were dispersed in a culture medium at the cell concentration of 2×10$^4$ cells/ml. The dispersion was seeded into a 24-well culture schale at 1 ml/well. Into this system, an ethanol solution which had been prepared by dissolving 1 α,25-dihydroxyvitamin $D_3$, or a compound of the present invention in ethanol so that it had a concentration of 1×10$^{-5}$ M, or 1×10$^{-4}$ M to 3×10$^{-3}$ M, respectively, was added at 1 μl/well (the final concentration: 1×10$^{-8}$ M in 1 α,25-dihydroxyvitamin $D_3$; and 1×10$^{-7}$ M to 3×10$^{-6}$ M in a compound of the present invention). As the control, ethanol was added at 1 μl/well. After culturing at 37° C. for 4 days in the presence of 5% $CO_2$, the cells were centrifugally collected.

(3) As the parameter of differentiation inducing effect on HL-60 cells, the induction of nitro blue tetrazolium (henceforth, NBT)-reducing activity was used. The NBT-reducing activity was determined according to the following procedure. That is, centrifugally collected cells were suspended in a fresh culture medium, and subsequently NBT and 12-O-tetradecanoylphorbol-13-acetate were added in such a manner that their concentrations became 0.1% and 100 ng/ml, respectively. After the mixed suspension was incubated at 37° C. for 25 min, a cytospin specimen was prepared. After air drying, it was stained with Kernechrot, and the ratio of the positive cells of NBT reduction activity was determined under an optical microscope. Percentage ratios of the positive cell ratio in a simultaneous treatment with 1 α,25-dihydroxyvitamin $D_3$ (1×10$^{-8}$ M) and a compound of the present invention at various treating concentrations (1×10$^{-7}$ to 3×10$^{-6}$ M) to that in a single treatment with 1 α,25-dihydroxyvitamin $D_3$ (1×10$^{-8}$ M) were plotted against treating concentrations of the compound of the present invention, and the treating concentration of the compound of the present invention at which the percentage ratio became 50% was determined as $IC_{50}$ value (nM). The results are shown in the following table.

NBT-reducing Activity Induction Effect on HL-60
Cell (Suppression Effect of Compounds of the
Present Invention on Cell Differentiation Induction
by 1 α,25-Dihydroxyvitamin $D_3$)

| $IC_{50}$ (nM) | Compound No. |
|---|---|
| <100 | 61a |
| 100 to 1000 | 51a, 62a, 63a, 81a, 101a |
| 1000 to 3000 | 71a |

This result shows that compounds of the present invention suppress cell differentiation induction caused by 1 α,25-dihydroxyvitamin $D_3$. That is, it has been shown that compounds of the present invention act as antagonists to 1 α,25-dihydroxyvitamin $D_3$.

Since Paget's disease of bone and hypercalcemia are caused by the acceleration of active vitamin $D_3$ activity, compounds of the present invention are useful as treating agents for these diseases. Further, since PTH increases with decreasing in-vivo concentration of active vitamin $D_3$, and has osteogenesis activity, compounds of the present invention are useful as treating agents for osteoporosis.

INDUSTRIAL FIELD OF APPLICATION

Compounds of the present invention can be used as active ingredients of pharmaceutical agents. Pharmaceutical compositions having a compound of the present invention can be used as agents for treating one or plurality of diseases selected from the group consisting of Paget's disease of bone, hypercalcemia and osteoporosis.

We claim a patent regarding the following inventions:

1. A vitamin $D_3$ derivative expressed by the following formula (1)

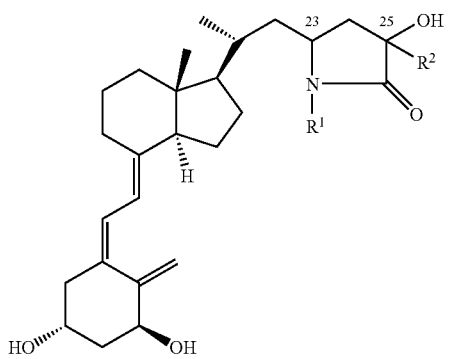

[wherein, $R^1$ is selected from an octyl group, a 3-phenylpropyl group, a 4-phenylbutyl group, a 2-naphthylmethyl group, and a 4-methoxybenzyl group], or a pharmaceutically permissible solvate thereof, wherein the solvent used to convert the vitamin $D_3$ derivative of formula (1) into a solvate is water, methanol, ethanol, 1-propanol, 2propanol, butanol, 2-methyl-2propanol, acetonitrile, acetone, methyl ethyl ketone, chloroform, ethyl acetate, diethyl ether, t-butyl methyl ether, benzene, toluene, DMF or DMSO.

2. The vitamin $D_3$ derivative or the pharmaceutically permissible solvate thereof according to claim 1, wherein $R^1$ is a 4-phenylbutyl group or a 4-methoxybenzyl group.

3. The vitamin $D_3$ derivative or the pharmaceutically permissible solvate thereof according to claim 1, wherein $R^2$ a methyl group, an ethyl group, a propyl group or a benzyl group.

4. The vitamin $D_3$ derivative or the pharmaceutically permissible solvate thereof according to claim 1, wherein $R^1$ is a 4-phenylbutyl group and $R^2$ is a methyl group.

5. The vitamin $D_3$ derivative or the pharmaceutically permissible solvate thereof according to claim 1, wherein $R^1$ is a 4-methoxybenzyl group and $R^2$ is a methyl group.

6. The vitamin $D_3$ derivative or the pharmaceutically permissible solvate thereof according to claim 1, wherein configurations of the 23-position and the 25-position in the above formula (1) are 23(R) configuration and 25(R) configuration, respectively.

7. The vitamin $D_3$ derivative or the pharmaceutically permissible solvate thereof according to claim 1, wherein configurations of the 23-position and the 25-position in the above formula (1) are 23(S) configuration and 25(S) configuration, respectively.

8. The vitamin $D_3$ derivative or the pharmaceutically permissible solvate thereof according to claim 1, wherein the vitamin $D_3$ derivative or the pharmaceutically permissible solvate thereof has a vitamin $D_3$ antagonist activity.

* * * * *